(12) United States Patent
Tada et al.

(10) Patent No.: US 7,508,201 B2
(45) Date of Patent: Mar. 24, 2009

(54) EDDY CURRENT SENSOR

(75) Inventors: Mitsuo Tada, Tokyo (JP); Yasunari Suto, Tokyo (JP)

(73) Assignee: Ebara Corporation, Tokyo (JP)

( * ) Notice: Subject to any disclaimer, the term of this patent is extended or adjusted under 35 U.S.C. 154(b) by 154 days.

(21) Appl. No.: 10/573,593

(22) PCT Filed: Oct. 18, 2004

(86) PCT No.: PCT/JP2004/015753

§ 371 (c)(1),
(2), (4) Date: Sep. 15, 2006

(87) PCT Pub. No.: WO2005/038391

PCT Pub. Date: Apr. 28, 2005

(65) Prior Publication Data

US 2007/0103150 A1 May 10, 2007

(30) Foreign Application Priority Data

Oct. 20, 2003 (JP) ............................. 2003-359938

(51) Int. Cl.
*G01B 7/06* (2006.01)
*G01R 33/12* (2006.01)
*G01N 27/72* (2006.01)

(52) U.S. Cl. ..................... 324/230; 324/229; 324/239

(58) Field of Classification Search ................ 324/222, 324/225, 228, 229, 230, 231, 239; 451/5, 451/8, 41, 285; 702/57, 170
See application file for complete search history.

(56) References Cited

U.S. PATENT DOCUMENTS

| | | | |
|---|---|---|---|
| 5,559,428 A | 9/1996 | Li et al. | |
| 5,644,221 A | 7/1997 | Li et al. | |
| 5,659,492 A | 8/1997 | Li et al. | |
| 5,660,672 A | 8/1997 | Li et al. | |
| 5,663,637 A | 9/1997 | Li et al. | |
| 5,770,948 A | 6/1998 | Li et al. | |
| 6,072,313 A * | 6/2000 | Li et al. | .................... 324/230 |
| 6,369,566 B1 * | 4/2002 | McClelland | ................ 324/229 |
| 6,499,336 B1 | 12/2002 | Raffer | |

(Continued)

FOREIGN PATENT DOCUMENTS

JP 7-294239 11/1995

(Continued)

*Primary Examiner*—Reena Aurora
*Assistant Examiner*—Kenneth J. Whittington
(74) *Attorney, Agent, or Firm*—Wenderoth, Lind & Ponack, L.L.P.

(57) ABSTRACT

An eddy current sensor (10) has a sensor coil (100) disposed near a conductive film (6) formed on a semiconductor wafer (W) and a signal source (124) configured to supply an AC signal to the sensor coil (100) to produce an eddy current in the conductive film (6). The eddy current sensor (10) includes a detection circuit operable to detect the eddy current produced in the conductive film (6). The detection circuit is connected to the sensor coil (100). The eddy current sensor (10) also includes a housing (200) made of a material having a high magnetic permeability. The housing (200) accommodates the sensor coil (100) therein. The housing (200) is configured so that the sensor coil (100) forms a path of a magnetic flux (MF) so as to effectively produce an eddy current in the conductive film (6).

26 Claims, 14 Drawing Sheets

U.S. PATENT DOCUMENTS

| | | |
|---|---|---|
| 6,563,308 B2 | 5/2003 | Nagano et al. |
| 6,707,540 B1 | 3/2004 | Lehman et al. |
| 7,046,001 B2 | 5/2006 | Tada et al. |
| 2002/0047705 A1 | 4/2002 | Tada et al. |
| 2004/0032256 A1 | 2/2004 | Tada et al. |
| 2004/0189290 A1* | 9/2004 | Lehman et al. ............. 324/230 |
| 2005/0017712 A1* | 1/2005 | Le ............................ 324/230 |

FOREIGN PATENT DOCUMENTS

| | | |
|---|---|---|
| JP | 07-294239 | 11/1995 |
| JP | 10-78336 | 3/1998 |
| JP | 11-256987 | 9/1999 |
| JP | 2001-141529 | 5/2001 |
| JP | 2003-106805 | 4/2003 |

* cited by examiner

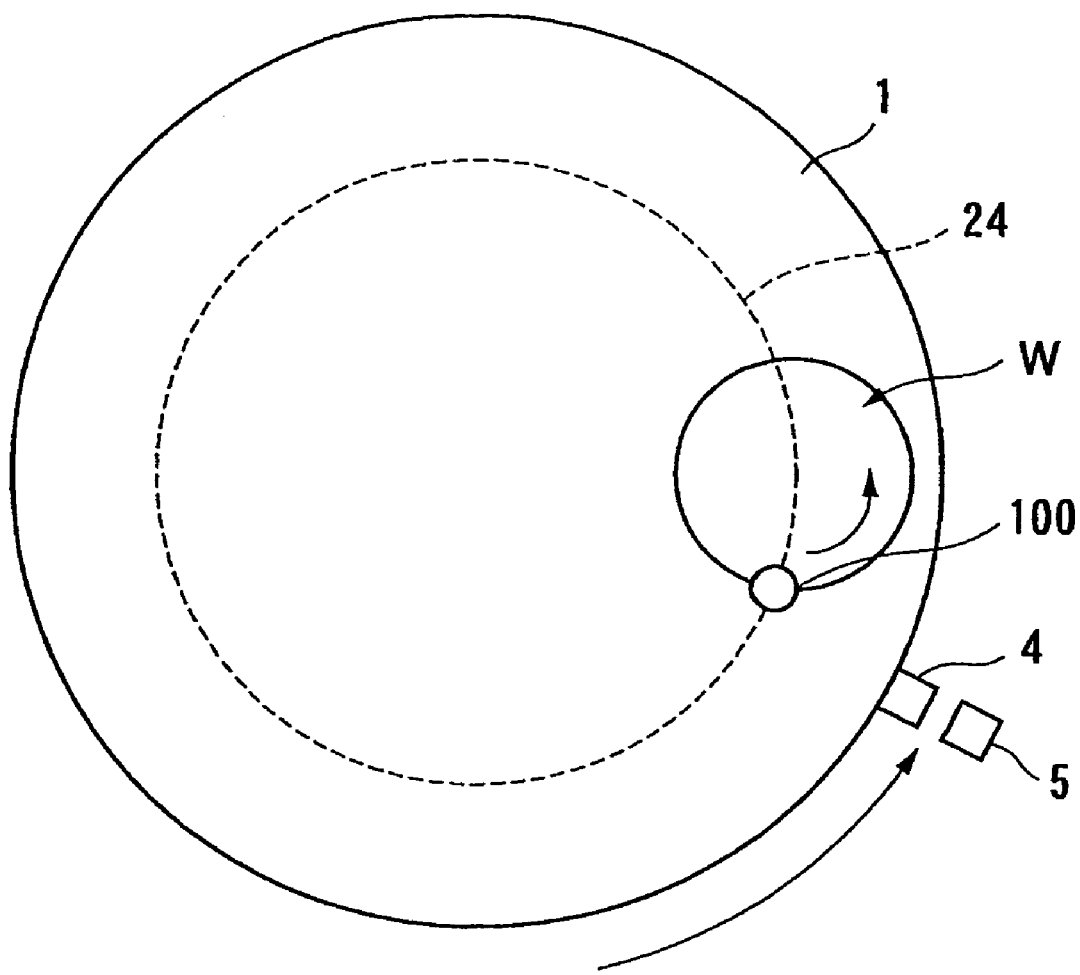
F I G. 3

F I G. 14A
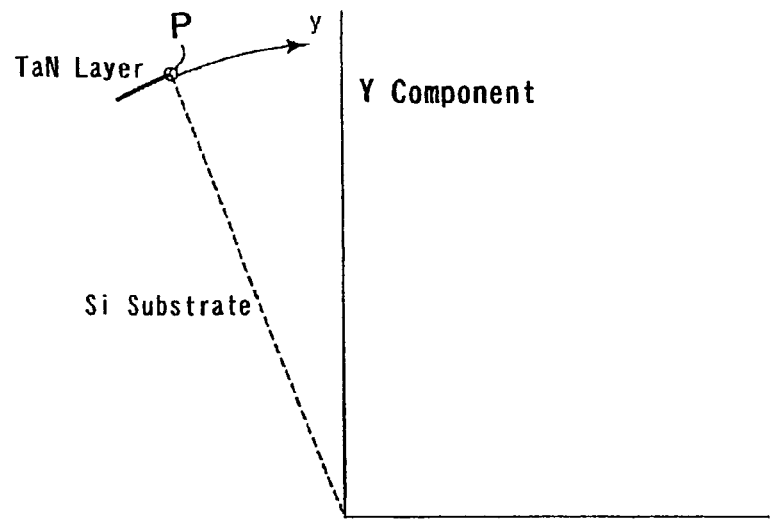
F I G. 14B
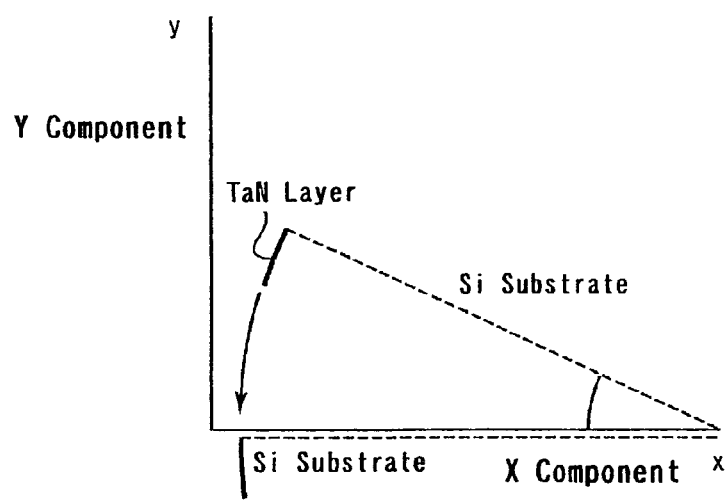
F I G. 14C
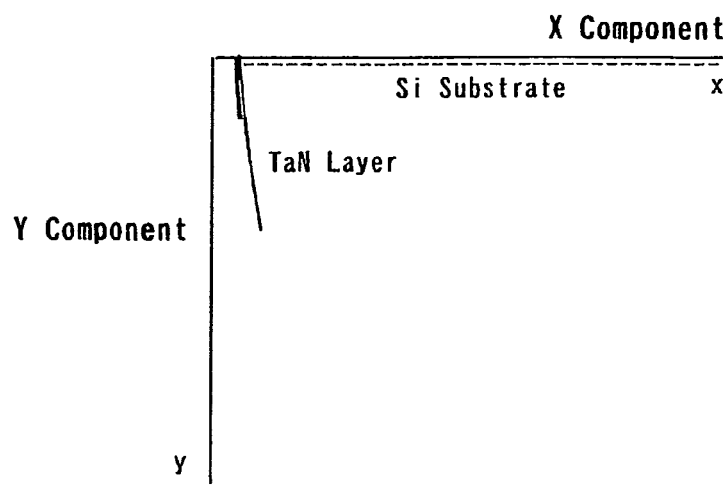

F I G. 2 2
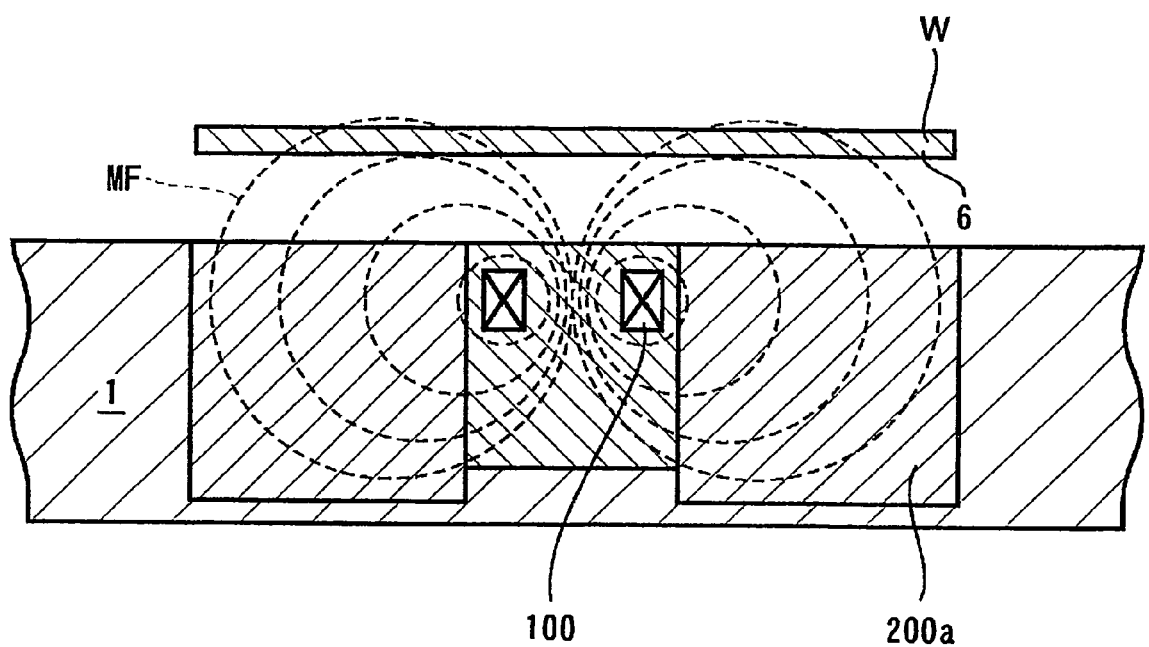

EDDY CURRENT SENSOR

TECHNICAL FIELD

The present invention relates to an eddy current sensor, and more particularly to an eddy current sensor suitable for detecting the thickness of a conductive film formed on a surface of a substrate such as a semiconductor wafer. The present invention also relates to a substrate processing apparatus, such as a polishing apparatus or a substrate deposition apparatus, having such an eddy current sensor.

BACKGROUND ART

In order to form interconnection circuits in a substrate such as a semiconductor wafer, there has been employed a process of plating a substrate with copper to form a copper layer thereon, and then removing unnecessary portions of the copper layer by chemical mechanical polishing (CMP) to form a copper interconnection layer in the substrate. During the chemical mechanical polishing (CMP) in such a process, it is necessary to accurately control the progress of the polishing process of the copper layer (the film thickness of the copper layer). An optical sensor or an eddy current sensor may be employed to control the film thickness of such a conductive film.

An optical sensor measures the film thickness of a conductive film based on the wavelength of light. Accordingly, it is possible to perform accurate measurement of the film thickness in areas to which light is applied. For example, in order to detect the film thickness of a conductive film formed on a semiconductor substrate during chemical mechanical polishing, it is necessary to form an opening at a position through which light is applied directly to the substrate during polishing. However, such formation of an opening may adversely affect polishing performance of the chemical mechanical polishing apparatus.

An eddy current sensor measures the film thickness of a conductive film based on the magnitude of an eddy current produced in the conductive film. Accordingly, for example, an eddy current sensor can be mounted in a polishing tool of a chemical mechanical polishing apparatus. Further, an eddy current sensor can measure polishing conditions of a semiconductor substrate in a non-contact manner during polishing. Thus, the polishing tool is not required to have an opening to observe the substrate. For example, the film thickness (the amount of polishing) of a conductive film formed on a semiconductor substrate can be measured in a non-contact manner during polishing without any windows being formed in a polishing pad. Furthermore, there has been proposed an eddy current sensor capable of detecting an endpoint of a polishing process of an ultrathin film such as a barrier layer.

However, when a sensor coil of an eddy current sensor is embedded in a polishing table made of a conductive material such as stainless, a magnetic flux generated by the sensor coil produces an eddy current in the polishing table. Accordingly, a magnetic flux externally emitted is lessened. In such a case, since a magnetic flux that reaches a semiconductor wafer to be measured is lessened, an eddy current produced in the conductive film on the wafer is also reduced. Accordingly, an eddy current sensor is required to have a high sensibility.

For example, in a case where an eddy current sensor is provided in a polishing apparatus, a polishing pad is disposed between a conductive film of a semiconductor substrate and a sensor coil of the eddy current sensor. If measurement environment such as the thickness of the polishing pad changes, then signals from the eddy current sensor also change. Thus, the eddy current sensor is required to measure the film thickness of the substrate in consideration of such measurement environment as one of parameters. Accordingly, complicated and troublesome processes are required to measure the film thickness of the substrate.

When an ultrathin conductive film is measured, an eddy current produced inside of a substrate such as a semiconductor wafer is not negligible. Accordingly, in order to measure the film thickness of the ultrathin conductive film, influence from the interior of the substrate should be considered as a measurement environment which would adversely affect measurement with the eddy current sensor. Thus, complicated and troublesome processes are required to measure the film thickness of the substrate.

SUMMARY OF INVENTION

The present invention has been made in view of the above drawbacks. It is, therefore, an object of the present invention to provide an eddy current sensor which is unlikely to be influenced from a measurement environment, and can readily measure a conductive film with high accuracy.

According to a first aspect of the present invention, there is provided an eddy current sensor having a sensor coil disposed near a conductive film formed on a substrate and a signal source configured to supply an AC signal to the sensor coil to produce an eddy current in the conductive film. The eddy current sensor includes a detection circuit operable to detect the eddy current produced in the conductive film. The detection circuit is connected to the sensor coil. The eddy current sensor also includes a housing made of a material having a high magnetic permeability. The housing accommodates the sensor coil therein. Thus, the housing is configured so that the sensor coil forms a path of a magnetic flux so as to effectively produce an eddy current in the conductive film.

With the above arrangement, a magnetic flux from the sensor coil forms a path (magnetic circuit) so as to pass through the housing having a high magnetic permeability, which is located around the sensor coil and then pass through the conductive film to be measured. Since the magnetic flux does not pass through a member in an installation environment, the magnetic flux is not attenuated. Thus, an eddy current can effectively be produced in the conductive film by the sensor coil, and the film thickness of the conductive film can be measured with high sensitivity.

The housing may be formed into a cylindrical shape or a shape surrounding the sensor coil. The sensor coil may include an excitation coil operable to produce an eddy current in the conductive film and a detection coil operable to detect the eddy current produced in the conductive film. The sensor coil may further include a balance coil operable to adjust a zero point of a detection output in cooperation with the detection coil. By adjusting the zero point, it is possible to amplify only a variation signal corresponding to the thickness of the conductive film. The housing may be disposed within a conductive member (polishing table).

According to a second aspect of the present invention, there is provided an eddy current sensor having a sensor coil disposed near a conductive film formed on a substrate and a signal source configured to supply an AC signal to the sensor coil to produce an eddy current in the conductive film. The eddy current sensor includes a detection circuit operable to detect the eddy current produced in the conductive film. The detection circuit is connected to the sensor coil. The eddy current sensor also includes an insulating member accommodating the sensor coil therein. The insulating member is embedded in a conductive material (polishing table).

According to a third aspect of the present invention, there is provided an eddy current sensor having a sensor coil disposed near a conductive film formed on a substrate and a signal source configured to supply an AC signal to the sensor coil to produce an eddy current in the conductive film. The eddy current sensor includes a detection circuit operable to detect the eddy current produced in the conductive film based on an impedance as viewed from the sensor coil. The eddy current sensor also includes a controller configured to specify a point including a resistance component and a reactance component of the impedance in rectangular coordinates and to detect film thickness of the conductive film from an angle formed by a line connected between the point and the a predetermined central point in the rectangular coordinates. The controller may be configured to detect the film thickness of the conductive film from the angle without influence due to a distance between the sensor coil and the conductive film. The predetermined central point may be calibrated as a point at which the film thickness of the conductive film can be obtained without influence due to the distance between the sensor coil and the conductive film by a calibration data table including film thicknesses and resistance components (Xm) and reactance components (Ym) corresponding to the film thicknesses.

When preliminary measurement lines are drawn on xy-coordinates based on output values of resistance components and reactance components of the same film thickness of the conductive film with respect to different measurement environments, the preliminary measurement lines intersect each other at a single intersection (central point) irrespective of the measurement environments. When the film thickness of a conductive film is measured under an unknown measurement environment, the intersection and a point having output values of a resistance component and a reactance component of an eddy current signal produced in the conductive film are connected on the xy-coordinates by an actual measurement line. By comparing a slope of the actual measurement line (an angle between the actual measurement line and a base line) to slopes of the preliminary measurement lines (angles between the preliminary measurement lines and the base line), the film thickness of the conductive film can readily be obtained. Thus, the eddy current sensor can readily and quickly measure the film thickness of the conductive film without influence of the thickness of a polishing pad.

According to a fourth aspect of the present invention, there is provided an eddy current sensor having a sensor coil disposed near a first conductive film formed on a substrate and a signal source configured to supply an AC signal to the sensor coil to produce an eddy current in the first conductive film. The eddy current sensor includes a detection circuit operable to detect the eddy current produced in the first conductive film based on an impedance as viewed from the sensor coil. The eddy current sensor also includes a controller configured to specify first impedance coordinates of a resistance component and a reactance component of the impedance in rectangular coordinates and to perform phase rotation, parallel displacement, and expansion on the first impedance coordinates.

The controller may be configured to perform phase rotation to conform second impedance coordinates of an impedance of a second conductive material to an axis of the rectangular coordinates and expansion to obtain a change of the first impedance coordinates of the impedance of the first conductive material in an enlarged manner when the first impedance coordinates are influenced by the second impedance coordinates.

A phase rotation angle is obtained to conform output values of a resistance component and a reactance component of an eddy current produced in the second conductive material (substrate) to an x-axis or a y-axis in xy-coordinates. When the film thickness of a conductive film is measured, output values of a resistance component and a reactance component of a measured eddy current are subjected to phase rotation of the phase rotation angle. Thus, the resistance component and the reactance component of the eddy current produced in the second conductive material can be cancelled. Accordingly, the eddy current sensor can accurately measure the film thickness of the first conductive film without influence from the second conductive film. The phase rotation is more effective in a case where the first conductive film is so thin as to be influenced by the second conductive film. Such phase rotation can be performed only when precise measurement is required. Thus, the phase rotation can avoid troublesome processes for film thickness measurement.

The second conductive film may comprise a semiconductor wafer, and the first conductive film may comprise a barrier layer or a metal film formed on the semiconductor wafer.

According to a fifth aspect of the present invention, there is provided an eddy current sensor having a sensor coil disposed near a conductive film formed on a substrate and a signal source configured to supply an AC signal to the sensor coil to produce an eddy current in the conductive film. The eddy current sensor includes a detection circuit operable to detect the eddy current produced in the conductive film based on an impedance as viewed from the sensor coil. The eddy current sensor also includes a storage device operable to store a correction coefficient according to a deposition condition of the conductive film and a controller configured to specify a point including a resistance component and a reactance component of the impedance in rectangular coordinates and to correct the point by the correction coefficient stored in the storage device.

Individual differences of the eddy current sensor can be cancelled by measuring the film thickness of a reference wafer having a conductive film, and adjusting a base point and an end point on an arc locus of the film thickness in impedance coordinates to desired coordinates (x, y). The controller may be configured so that the resistance component and the reactance component are constant when film thickness of a reference conductive film is measured.

According to a sixth aspect of the present invention, there is provided an eddy current sensor having a sensor coil disposed near a conductive film formed on a substrate and a signal source configured to supply an AC signal to the sensor coil to produce an eddy current in the conductive film. The eddy current sensor includes a detection circuit operable to detect the eddy current produced in the conductive film based on an impedance as viewed from the sensor coil. The eddy current sensor also includes a controller configured to specify an impedance coordinates of a resistance component and a reactance component of the impedance in rectangular coordinates and to move the impedance coordinates on a semicircular locus in the rectangular coordinates according to progress of a process.

Thus, the controller specifies impedance coordinates of a resistance component and a reactance component of the impedance in rectangular coordinates. A locus of the impedance coordinates moves on the semicircular locus in the rectangular coordinates according to progress of the process. The controller may be configured to calculate a change of the film thickness of the conductive film based on the length of an arc on which the impedance coordinates move. The change of the film thickness of the conductive film can be calculated from the length (arc length) of the arc on which the impedance coordinates move. The eddy current sensor can be configured so that the length of the arc is not influenced by conductivity of the substrate, which is located below the conductive film. For example, even if the underlying silicon substrate is a low-resistance substrate, the film thickness of the conductive film having a high resistance such as a metal film or a barrier layer can be detected without influence from the underlying silicon substrate.

The impedance may dramatically vary along one of axes in the rectangular coordinates. In this case, the controller may be configured to select the one of axes in the rectangular coordinates. The impedance coordinates may be configured to be set by an offset, an amplification degree, phase rotation, or polarity selection of a main amplifier.

The controller may be configured to measure the impedance coordinates every predetermined time and to detect an endpoint of a process based on a correlation between an impedance characteristic and model data. The controller may be configured to predict a remaining time until an endpoint of a process. Thus, it is possible to monitor progress of the (polishing) process and to promptly cope with anomaly caused during the (polishing) process for preventive maintenance.

It is desirable that a substrate holding device has a conductive member located away from the sensor coil so as not to have an influence on the eddy current produced in the conductive film.

According to a seventh aspect of the present invention, there is provided an eddy current sensor having a sensor coil disposed near a substrate having a plurality of zones and a signal source configured to supply an AC signal to the sensor coil to produce an eddy current in the substrate. The eddy current sensor includes a detection circuit operable to obtain signal data on the eddy current produced in the plurality of zones of the substrate. The eddy current sensor also includes a controller configured to detect an endpoint of a process based on the signal data.

The controller may be configured to employ a determination value including a value of signal data on an optimum zone of the plurality of zones, an average value of the signal data on the plurality of zones, an average value of the signal data on a desired combination of the plurality of zones, an effective value, a first time-derivative of the signal data, a second time-derivative of the signal data, and a nth time-derivative of the signal data. Further, the controller may be configured to compare the determination value with a predetermined value to detect the endpoint of the process.

The controller may be configured to perform an edge cutting process on the signal data. The signal data may include X and Y components of an impedance, a phase θ, a synthesis impedance Z, a frequency F, and a film thickness value converted therefrom. The controller may be configured to perform an arithmetical operation on a reference time, which is calculated from the signal data, with a coefficient to calculate an additional period of process time and add the additional period of process time to the reference time so as to detect the endpoint of the process.

According to an eighth aspect of the present invention, there is provided a substrate processing apparatus having a processing device configured to process the substrate and the aforementioned eddy current sensor.

According to a ninth aspect of the present invention, there is provided a polishing apparatus having a polishing surface, a substrate holding device configured to hold the substrate and press the substrate against the polishing surface, and the aforementioned eddy current sensor.

According to a tenth aspect of the present invention, there is provided a substrate deposition apparatus having a substrate deposition device configured to deposit a conductive film on the substrate, and the aforementioned eddy current sensor.

According to the present invention, it is possible to avoid adverse influence from a measurement environment and to readily and quickly measure the film thickness of a conductive film with high accuracy.

The above and other objects, features, and advantages of the present invention will be apparent from the following description when taken in conjunction with the accompanying drawings which illustrate preferred embodiments of the present invention by way of example.

BRIEF DESCRIPTION OF DRAWINGS

FIG. 3 is a plan view showing a relationship between a semiconductor wafer held by a top ring of the polishing apparatus and a sensor coil of the eddy current sensor shown in FIG. 1;

FIGS. 14A through 14C are diagrams showing that impedance components of a silicon substrate is cancelled by phase rotation, and that components of a TaN film are expanded;

FIG. 22 is a cross-sectional view showing a magnetic flux distribution by an eddy current sensor according to another embodiment of the present invention;

DETAILED DESCRIPTION OF PREFERRED EMBODIMENTS

A polishing apparatus having an eddy current sensor according to embodiments of the present invention will be described below with reference to FIGS. 1 through 23.

Figure 1:
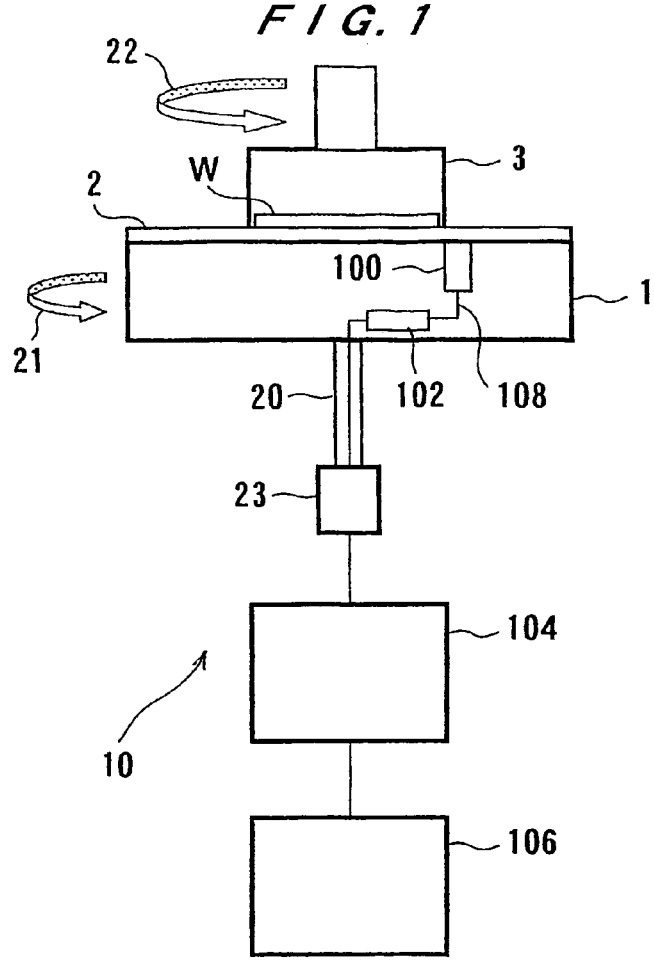
FIG. 1 is a schematic diagram showing a polishing apparatus having an eddy current sensor according to a first embodiment of the present invention.

FIG. 1 shows a polishing apparatus having an eddy current sensor 10 according to a first embodiment of the present invention. As shown in FIG. 1, the polishing apparatus has a polishing table 1, a polishing pad 2 attached to a surface of the polishing table 1, a top ring 3 for holding a semiconductor wafer W and pressing the semiconductor wafer W against the polishing pad 2, and an eddy current sensor 10 for measuring the film thickness of a conductive film, which is to be polished, on the semiconductor wafer W. The polishing table 1 of the polishing apparatus is rotatable about a support shaft 20 as shown by an arrow 21. The top ring 3 is rotatable about its axis as shown by an arrow 22.

The top ring 3 presses the semiconductor wafer W against the polishing pad 2 on the polishing table 1 while the top ring 3 and the polishing table 1 are rotated independently of each other. At that time, a polishing liquid is supplied onto the polishing pad 2 from a polishing liquid supply nozzle (not shown). Thus, the semiconductor wafer W is polished. In the present embodiment, the polishing table 1 of the polishing apparatus is made of a ceramic material such as SiC or a metal material such as stainless (SUS).

As shown in FIG. 1, the eddy current sensor 10 includes a sensor coil 100 embedded in the polishing table 1, a preamplifier 102, a main amplifier 104, and a controller 106. Although the sensor coil 100 and the preamplifier 102 are separated in the illustrated example, a preamplifier may be incorporated integrally into the sensor coil 100. A cable 108 extends from the sensor coil 100 through the support shaft 20 of the polishing table 1. Thus, the sensor coil 100 is connected to the controller 106 through a rotary joint 23, which is provided at an end of the support shaft 20, and the main amplifier 104.

The controller 106 of the eddy current sensor 10 includes an analog filter, such as a low-pass filter (LPF), a band-pass filter (BPF), a high-pass filter (HPF), or a notch filter, or a digital filter using software to remove noise in sensor signals. Each filter may have a suitable cut-off frequency. For example, when the low-pass filter has a cut-off frequency of 0.1 to 1 kHz, noise included in sensor signals can be removed during polishing so as to accurately measure the film thickness of the semiconductor wafer W.

Figure 2:
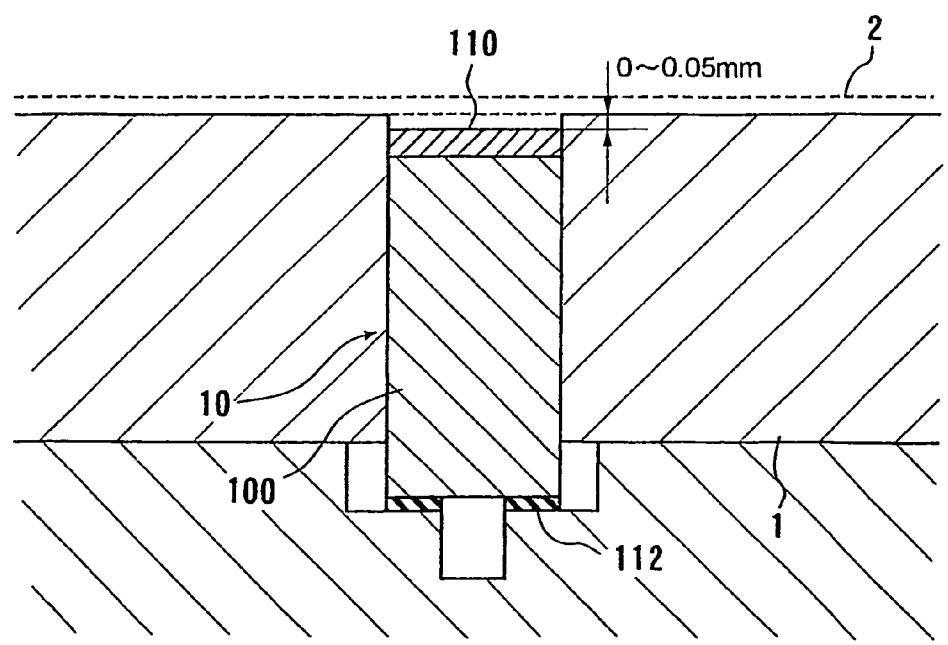
FIG. 2 is an enlarged cross-sectional view showing a sensor coil of the eddy current sensor shown in FIG. 1.

FIG. 2 is an enlarged cross-sectional view showing the sensor coil 100 of the eddy current sensor 10. The polishing pad 2 is attached to an upper surface of the polishing table 1. As shown in FIG. 2, a fluororesin 110 is attached to an upper end face of the sensor coil 100 near the polishing pad 2. The fluororesin 110 can prevent the sensor coil 100 from being removed together with the polishing pad 2 when the polishing pad 2 is peeled off from the polishing table 1. The fluororesin 110 has an upper end face located 0 to 0.05 mm below the upper surface of the polishing table 1 so that the polishing pad 2 does not swell at a position above the sensor coil 100. Thus, a polishing process is not affected by the presence of the sensor coil 100. The height difference between the upper surface of the polishing table 1 and the upper end face of the sensor coil 100 should preferably be as small as possible. For example, the height difference can practically be set around 0.01 mm. The height of the sensor coil 100 can be adjusted by a shim (thin plate) 112 provided at a lower end of the sensor coil 100 or by a screw (not shown).

The rotary joint 23 interconnecting the sensor coil 100 and the controller 106 can transmit signals even though it has a rotating member. However, the rotary joint 23 has a limited number of signal lines to transmit signals. In the present embodiment, the rotary joint 23 can have only eight signal lines for a DC voltage source, output signals, and various control signals. One signal line can transmit control signals including discriminant DC voltages, modulation frequencies, 1-bit digital signals, and the like from the controller 106 through the rotary joint 23 to the preamplifier 102. The preamplifier 102 has an input part operable to process the control signals. For example, according to command signals on coil balance in the sensor coil 100 and properties of a film to be polished, oscillation frequencies of the preamplifier 102 can be adjusted in a range of 2 to 8 MHz. The gain of the amplification of the RF voltage can also be adjusted. The aforementioned limitation on the number of the signal lines can be eliminated by using wireless signal transmission.

FIG. 3 is a plan view showing a relationship between the semiconductor wafer W held by the top ring 3 and the sensor coil 100 of the eddy current sensor 10 which is embedded in the polishing table 1. As shown in FIG. 3, a dog 4 is provided at a periphery of the polishing table 1, and a dog sensor 5 is provided so as to correspond to the dog 4. The dog sensor 5 detects the dog 4 and accordingly detects the rotation of the polishing table 1. Signal processing for the semiconductor wafer W held by the top ring 3 is started based on the detection signals from the dog sensor 5. Specifically, the sensor coil 100 of the eddy current sensor 10 scans the semiconductor wafer W on a trace line 24 shown in FIG. 3 while the polishing table 1 is rotated.

While the polishing table 1 makes one revolution, the dog sensor 5 detects the dog 4 and outputs a detection signal to the eddy current censor 10. At that time, because the sensor coil 100 is not yet located below the semiconductor wafer W, a sensor signal from the sensor coil 100 of the eddy current sensor 10 represents sensing results of the exterior of the wafer W. When the sensor coil 100 is moved to an area below the semiconductor wafer W, the controller 106 of the eddy current sensor 10 receives a sensor signal having a level corresponding to an eddy current produced in the conductive film of the wafer W. After the sensor coil 100 passes the area below the semiconductor wafer W, the controller 106 of the eddy current sensor 10 receives a sensor signal having such a level that no eddy current is produced, i.e., a sensor signal representing sensing results of the exterior of the wafer W.

In this case, the sensor coil 100 may be configured to continuously perform sensing. However, since levels of sensor signals received by the controller 106 vary according to changes of the film thickness of the wafer W during polishing, timing of measurement becomes unstable if the film thickness of the conductive film on the semiconductor wafer W is simply sensed by the sensor coil 100. Accordingly, it is desirable to obtain and set a level of a sensor signal when to start measurement on a polishing area of the semiconductor wafer W. For example, timing of measurement may be obtained by water-polishing a reference wafer (dummy wafer) while supplying water from the polishing liquid supply nozzle (not shown). Specifically, a reference wafer, which has a copper layer of 1000 nm deposited thereon, may be water-polished on the polishing table 1, which is rotated at a rotational speed of 60 min$^{-1}$, for 120 seconds.

More specifically, a median value of sensor signal values is calculated from sensor signals with respect to the exterior and interior of the semiconductor wafer W after the controller 106 receives the detection signal of the dog 4 from the dog sensor 5. The calculated median value is set as a criterion level for measurement of the semiconductor wafer W. Thus, once the controller 106 receives a sensor signal having a level higher than the criterion level after receiving the detection signal of the dog 4 from the dog sensor 5, sensor signals are acquired, for example, every 1 millisecond. The acquisition of the sensor signals is ended when the sensor coil 100 is moved apart from the wafer W. The acquired sensor signals are allocated to respective regions according to the physical dimension of the wafer W. Further, validation and invalidation of sensor signals may be set in the system. For example, invalidation of sensor signals may be set when no polishing process is performed, when levels of sensor signals are higher than a predetermined value, when levels of sensor signals are lower than a predetermined value, or when the top ring 3 is not present above the sensor coil 100.

In the eddy current sensor 10, the sensor coil 100, which is located near the conductive film, passes a magnetic flux through the conductive film of the wafer so as to produce an eddy current in the conductive film. The film thickness of the conductive film is measured based on a sensor signal caused by the eddy current. Accordingly, the eddy current sensor 10 can measure the film thickness of the conductive film without any windows being formed in the polishing pad 2 on the polishing table 1 by embedding the sensor coil 100 in the polishing table 1.

For example, the film thickness of the conductive film is monitored from the beginning of the polishing by the eddy current sensor according to the present invention. Thus, by the eddy current sensor, the film thickness of the conductive film can continuously or intermittently be monitored in real time from the beginning to the end of the polishing. This feature facilitates change or addition of the polishing process. Continuous measurement means measurement performed by an apparatus in which an eddy current sensor continuously faces a semiconductor substrate having a conductive film formed thereon (see FIGS. 23 and 24). Intermittent measurement means measurement performed by an apparatus in which an eddy current sensor periodically faces a semiconductor substrate having a conductive film formed thereon (see FIGS. 1 and 3).

Further, for example, after the controller 106 of the eddy current sensor 10 receives a signal representing that the film thickness of a tungsten film formed on a wafer becomes 1000 Å, the polishing process may quickly be switched into a low-pressure process in which the wafer is pressed against the polishing pad under a low pressure. Further, the polishing process can be controlled and changed in various manners in real time based on the absolute film thickness which has been measured. For example, water-polishing may be conducted to lower the temperature of the polishing table and the polishing rate. Alternatively, slurry to be supplied onto the polishing pad may be changed into slurry having a low polishing rate. Such a process control based on sensor signals of the eddy current sensor can reduce the amounts of dishing and erosion. As a matter of course, such a process control using the eddy current sensor can be applied not only to tungsten polishing, but also to copper polishing and aluminum polishing.

In the case of tungsten polishing, when a sensor signal from the eddy current sensor represents a film thickness of 1000 Å, 500 Å, or 0 Å, the aforementioned change of polishing conditions may be conducted to achieve various types of process management. Alternatively, the polishing conditions may be changed when a required amount of polishing is outputted as the film thickness. In the case of copper polishing, when a sensor signal from the eddy current sensor represents a film thickness of 1500 Å, the polishing conditions may be changed.

There will be described specific examples of a measurement process of the film thickness of a conductive film with an eddy current sensor according to the present invention.

Figure 4:
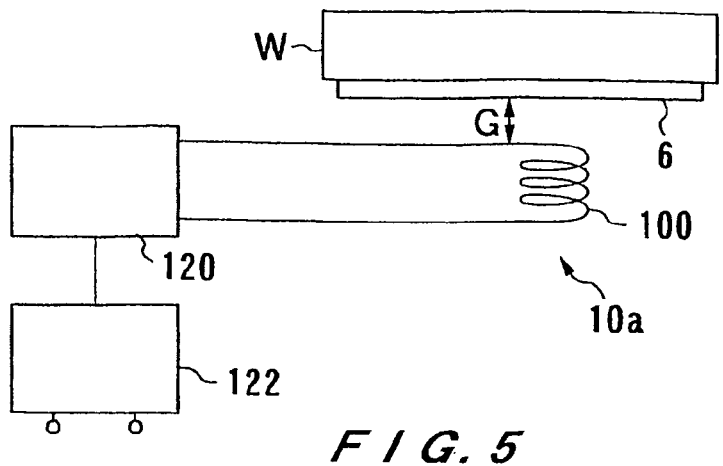
FIG. 4 is a block diagram showing an example of a frequency-type eddy current sensor used as the eddy current sensor according to the first embodiment of the present invention.

The aforementioned eddy current sensor 10 is classified into two types of eddy current sensors including a frequency-type eddy current sensor which produces an eddy current in a conductive film and detects the film thickness based on changes in varied oscillation frequency, and an impedance-type eddy current sensor which varies an impedance as viewed from a sensor coil to a conductive film and detects the film thickness based on changes in impedance. FIG. 4 is a diagram showing a frequency-type eddy current sensor 10a, whereas FIG. 5 is a diagram showing an impedance-type eddy current sensor 10b.

As shown in FIG. 4, the frequency-type eddy current sensor 10a has a sensor coil 100 disposed near a conductive film 6 of a semiconductor wafer W to be measured, a variable-frequency Colpitts oscillator 120 (signal source) connected to the sensor coil 100, and a frequency divider/counter circuit 122 connected to the Colpitts oscillator 120. In this eddy current sensor 10a, the oscillation frequency of the Colpitts oscillator 120 varies when the film thickness of the conductive film 6 changes. Thus, changes of the film thickness of the conductive film 6 can be detected by the variation of the oscillation frequency of the Colpitts oscillator 120. The frequency divider/counter circuit 122 can detect the variation of the oscillation frequency of the Colpitts oscillator 120 and thus detect the changes of the film thickness of the conductive film 6. Specifically, the sensor coil 100 and the oscillator 120 form a tank circuit which oscillates at an oscillation frequency corresponding to the film thickness of the conductive film 6. Oscillation signals of the oscillator 120 are divided in frequency and counted by the frequency divider/counter circuit 122 to detect the oscillation frequency of the oscillator 120. The oscillation frequency of the oscillator 120 is converted into a corresponding film thickness.

Figure 5:
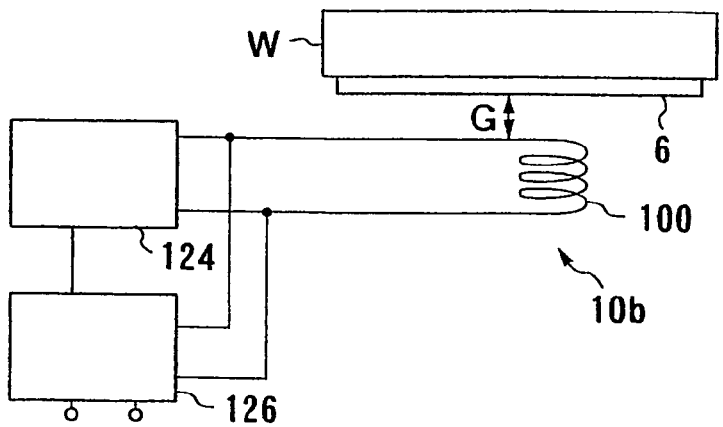
FIG. 5 is a block diagram showing an example of an impedance-type eddy current sensor used as the eddy current sensor according to the first embodiment of the present invention.

As shown in FIG. 5, the impedance-type eddy current sensor 10b has a sensor coil 100 disposed near a conductive film 6 of a semiconductor wafer W to be measured, an AC signal source 124 connected to the sensor coil 100, and a synchronous detection circuit 126 for detecting an impedance including the conductive film 6 as viewed from the sensor coil 100. The conductive film 6 formed on the semiconductor wafer W to be measured may be a copper plated film or an evaporated film of metal such as Au, Cr, or W, which has a thickness of about 0 to 2 μm, or a barrier layer formed as an underlying layer of the copper plated film or the evaporated film, which has a thickness of an angstrom order. The barrier layer is a high-resistance layer made of Ta, TaN, Ti, TiN, WN, or the like. It is important to detect the film thickness of a barrier layer in view of accurate detection of an endpoint of chemical mechanical polishing. The sensor coil 100 has one to several tens of turns of a coil. The sensor coil 100 is disposed near the conductive film 6, for example, at a distance of about 0.5 to 5 mm from the conductive film 6.

Figure 6:
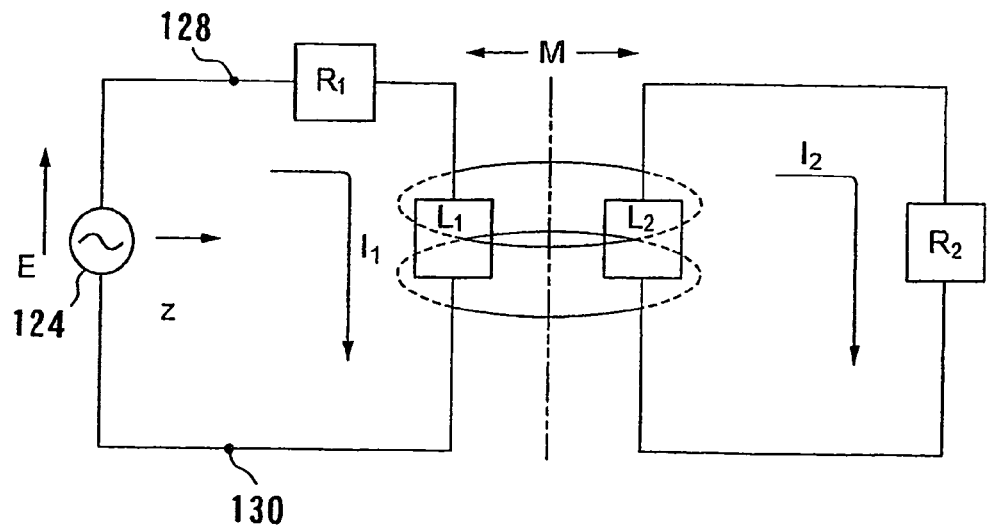
FIG. 6 is an equivalent circuit diagram of the eddy current sensor shown in FIG. 5.

FIG. 6 shows an equivalent circuit to the eddy current sensor 10b shown in FIG. 5. In the equivalent circuit shown in FIG. 6, because the oscillation frequency of the AC signal source 124 in the impedance-type eddy current sensor 10b is constant, an impedance z as viewed from the AC signal source 124 to the sensor coil 100 varies when the film thickness of the conductive film 6 changes. In the equivalent circuit shown in FIG. 6, $L_1$ represents a self-impedance of the sensor coil 100 (a primary self-impedance including the sensor coil 100), $R_1$ a resistance of the sensor coil 100 (a primary equivalent resistance including the sensor coil 100), and $I_1$ an current flowing through the sensor coil 100. With regard to the conductive film 6, $R_2$ represents an equivalent resistance corresponding to an eddy current loss, $L_2$ a self-impedance of the conductive film 6, and $I_2$ an eddy current flowing through the conductive film 6. The eddy current $I_2$ depends on the equivalent resistance $R_2$ of the conductive film 6 and the self-impedance $L_2$. The eddy current $I_2$ varies when the film thickness of the conductive film 6 changes. Accordingly, changes of the film thickness of the conductive film 6 can be detected via a mutual impedance M between the conductive film 6 and the sensor coil 100 by the variation of the impedance z as viewed from the AC signal source 124.

More specifically, the AC signal source 124 comprises an oscillator having a fixed frequency of 1 to 50 MHz, such as a quartz oscillator. When an AC voltage is supplied by the AC signal source 124, a current $I_1$ flows through the sensor coil 100. When a current flows through the sensor coil 100, which is disposed near the conductive film 6, an interlinkage of the magnetic flux with the conductive film 6 is caused so as to form a mutual impedance M between the sensor coil 100 and the conductive film 6. Thus, an eddy current $I_2$ flows through the conductive film 6. The impedance z as viewed from terminals 128 and 130 of the AC signal source 124 varies according to the magnitude of an eddy current loss caused in the conductive film 6.

The signal source of the eddy current sensor may employ a single radio wave, a mixed radio wave, an AM modulation radio wave, an FM modulation radio wave, a sweep frequency of a function generator, or oscillation frequencies of a plurality of signal sources. While the sensor faces the wafer being polished, balanced modulation, amplitude modulation, or pulse modulation is performed on an alternating burst electromagnetic field or a sine wave to thereby produce a magnetic field and a magnetic flux in the eddy current sensor. It is desirable to select an oscillation frequency and a modulation method which have a good sensitivity so as to conform to the type of the film to be measured.

Figure 7:
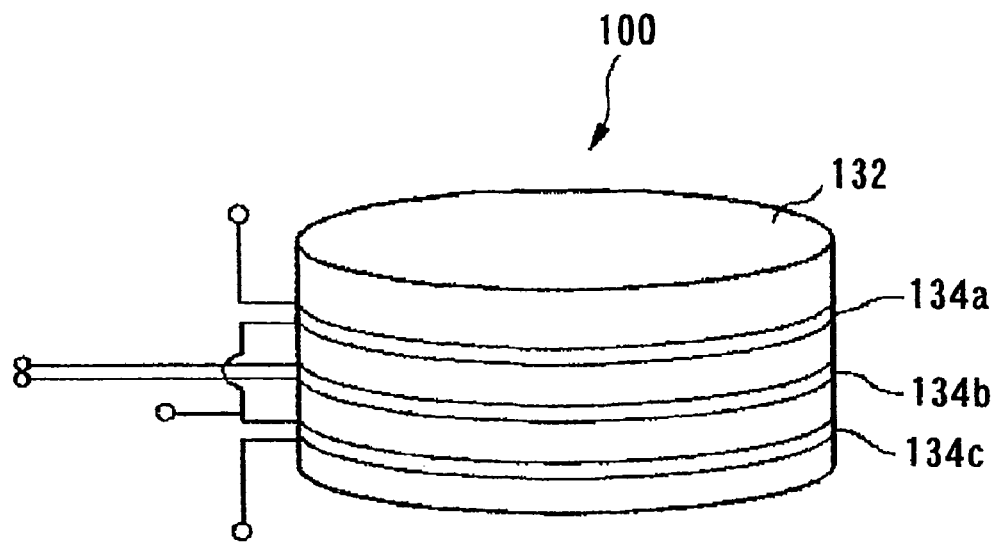
FIG. 7 is a perspective view showing an example of a sensor coil of the eddy current sensor according to the first embodiment of the present invention.

FIG. 7 shows an example of the sensor coil 100 according to the present embodiment. The sensor coil 100 has separated coils including a coil to form an eddy current in the conductive film and a coil to detect the eddy current in the conductive film. In the present embodiment, as shown in FIG. 7, the sensor coil 100 has three coils 134a, 134b, and 134c wound on a bobbin 132. The central coil 134b is an excitation coil connected to the AC signal source 124. The excitation coil 134b forms an eddy current in the conductive film 6 on the semiconductor wafer W located near the sensor coil 100 by a magnetic field, which is produced by a voltage supplied from the AC signal source 124. The detection coil 134a is disposed at an upper portion of the bobbin 132 (near the conductive film). The detection coil 134a detects a magnetic field produced by the eddy current formed in the conductive film. The balance coil 134c is disposed at the opposite side of the excitation coil 134b to the detection coil 134a.

Figure 8:
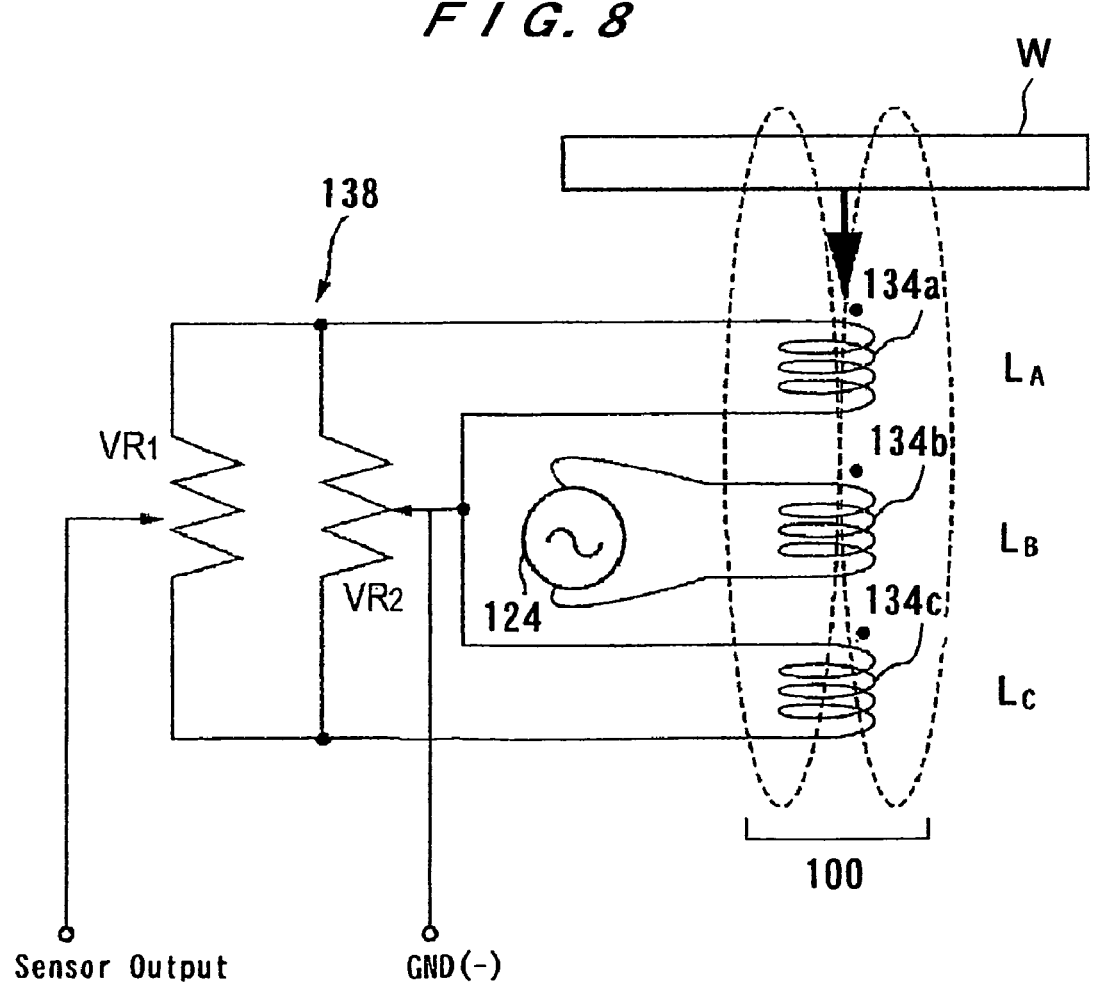
FIG. 8 is a circuit diagram showing connections of coils in the sensor coil shown in FIG. 7.
Figure 9:
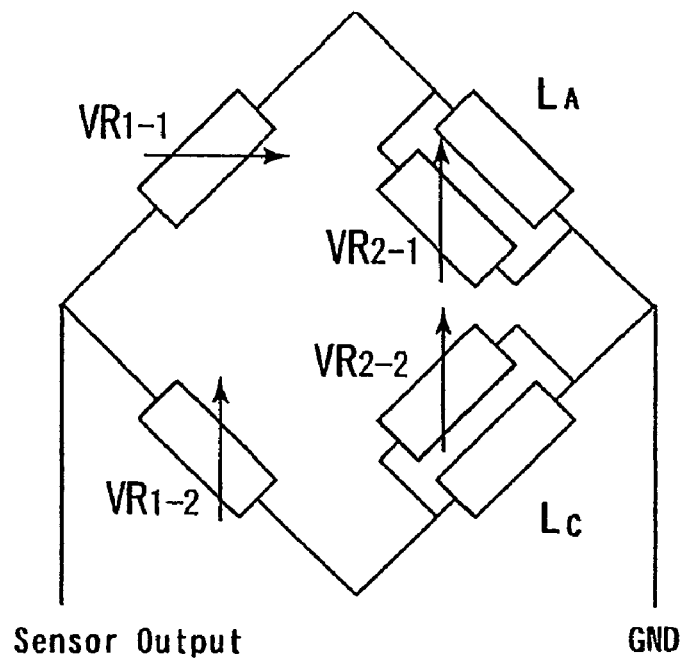
FIG. 9 is an equivalent circuit diagram of FIG. 8.

FIG. 8 shows an example of connections of the coils 134a, 134b, and 134c in the sensor coil 100. FIG. 9 shows an equivalent circuit of FIG. 8. In the present embodiment, the coil 134a, 134b, and 134c have the same number of turns (1 to 500 turns). The detection coil 134a and the balance coil 134c are connected in opposite phase to each other.

Thus, the detection coil 134a and the balance coil 134c forms a series circuit in opposite phase. Each end of the series circuit is connected to a resistance bridge circuit 138 including a variable resistance $VR_2$. The excitation coil 134b is connected to the AC signal source 124. The excitation coil 134b produces an alternating magnetic field and an eddy current in the conductive film 6 located near the excitation coil 134b. By adjusting resistance values of the variable resistances $VR_1$ and $VR_2$, an output voltage of the series circuit including the coils 134a and 134c can be adjusted so as to be zero when no conductive film is located near the sensor coil 100.

Figure 10:
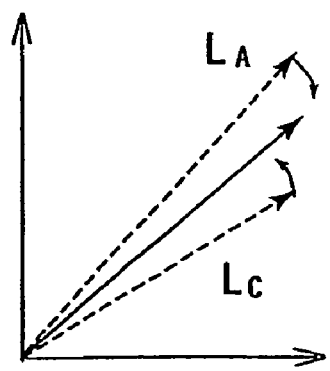
FIG. 10 is a vector diagram showing a voltage produced in a detection coil and a balance coil shown in FIG. 8.

Signals ($L_4$, $L_C$) of the coils 134a and 134c are adjusted by the variable resistances $VR_1$ and $VR_2$, which are connected in parallel to the coils 134a and 134c. The variable resistance $VR_2$ adjusts the signals so as to have the same phase, whereas the variable resistance $VR_1$ adjusts the lengths of the signals. Specifically, in the equivalent circuit shown in FIG. 9, the variable resistances $VR_1$ (=$VR_{1-1}$+$VR_{1-2}$) and $VR_2$ (=$VR_{2-1}$+$VR_{2-2}$) are adjusted so that $VR_{1-1} \times (VR_{2-2}+j\omega L_C) = VR_{1-2} \times (VR_{2-1}+j\omega L_4)$. Thus, as shown in FIG. 10, signals ($L_4$, $L_C$) of the coils 134a and 134c, which are illustrated by dashed lines, are adjusted into signals having the same phase and amplitude, which are illustrated by a solid line. The adjustment of the variable resistances $VR_1$ (=$VR_{1-1}$+$VR_{1-2}$) and $VR_2$ (=$VR_{2-1}$+$VR_{2-2}$) is, preferably automatically, conducted by a servomotor (DC pulse motor). Thus, balance can automatically be adjusted in consideration of some variations of the sensor coil 100 and environment in which the sensor coil 100 is provided, so that the eddy current sensor 10 has no individual differences.

Specifically, the series circuit of the detection coil 134a and the balance coil 134c is separated from the excitation coil 134b connected to the AC signal source 124. The balance is adjusted by the resistance bridge circuit 138. Accordingly, a zero point can be adjusted. Specifically, the balance coil 134c is operable to adjust a zero point of the detection output of the detection coil 134a. Thus, an eddy current flowing through the conductive film can be detected from zero, so that the detection sensitivity of an eddy current flowing through the conductive film can be enhanced. Accordingly, changes of the conductive film can be detected with high sensitivity based on the magnitude of an eddy current produced in the conductive film. When the conductive film is located near the detection coil 134a, a magnetic flux produced by an eddy current produced in the conductive film is interlinked with the detection coil 134a and the balance coil 134c. Since the detection coil 134a is located closer to the conductive film than the other coils, induced voltages produced by the coil 134a and 134c are unbalanced so as to detect the interlinkage magnetic flux formed by the eddy current in the conductive film.

Figure 11:
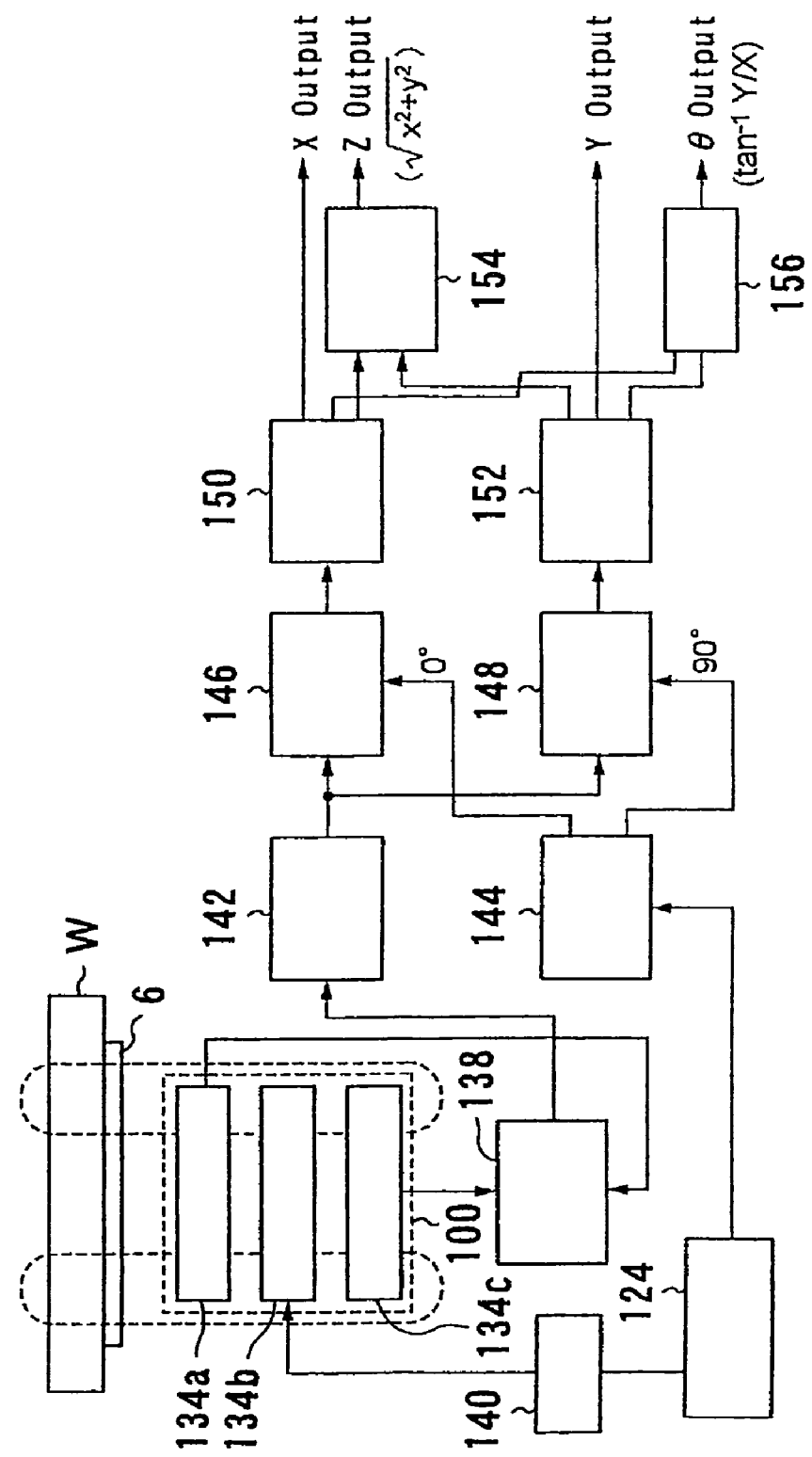
FIG. 11 is a block diagram showing a synchronous detection circuit connected to the sensor coil shown in FIG. 5.

FIG. 11 shows an example of the synchronous detection circuit 126 for measuring an impedance z as viewed from the AC signal source 124 to the sensor coil 100 shown in FIG. 5. In a measurement circuit shown in FIG. 11, it is possible to obtain a resistance component (R), a reactance component (X), an impedance component (Z), and a phase output ($\theta=\tan^{-1}R/X$) in the impedance plane coordinates (x, y) according to changes of the film thickness. Accordingly, with use of these signal outputs, the film thickness can be measured, for example, by the magnitudes of the respective components of the impedance. Thus, it is possible to detect the progress of the process in various manners. Hereinafter, the term "impedance" is used as meaning of both of a resistance component (R) and a reactance component (X).

As described above, the AC signal source 124, which supplies an AC signal to the sensor coil 100 located near the semiconductor wafer W having the conductive film 6 to be measured, comprises an oscillator having a fixed frequency, such as a quartz oscillator. For example, the AC signal source 124 supplies a voltage having a fixed frequency of 1 to 50 MHz. The AC voltage produced in the AC signal source 124 is supplied through a band-pass filter 140 to the excitation coil 134b of the sensor coil 100. Signals detected at the terminals of the sensor coil 100 are transmitted through a high-frequency amplifier 142 and a phase shift circuit 144 to a cosine synchronous detection circuit 146 and a sine synchronous detection circuit 148, which form a synchronous detection unit. The synchronous detection unit extracts a cosine component (X component) and a sine component (Y component) from the detection signals. The phase shift circuit 144 forms two signals of an in-phase component (0°) and a quadrature component (90°) from the oscillation signals formed in the signal source 124. The two signals are transmitted into the cosine synchronous detection circuit 146 and the sine synchronous detection circuit 148, respectively. Thus, the aforementioned synchronous detection is performed.

High-frequency components of at least 5 kHz, which are unnecessary, are removed from the signals-subjected to the synchronous detection by low-pass filters 150 and 152. Then, an X component output is obtained as an output of the cosine synchronous detection, and a Y component output is obtained as an output of the sine synchronous detection. Further, an impedance component $Z=(X^2+Y^2)^{1/2}$ is obtained from the X and Y component outputs by a vector arithmetic circuit 154. Similarly, a phase output ($\theta=\tan^{-1}Y/X$) is obtained from the X and Y component outputs by a vector arithmetic circuit ($\theta$ process circuit) 156. The filters are provided to remove noise components of the sensor signals. The filters have a cut-off frequency suitably set for their purposes.

Thus, the signal outputs X and Y, the phase $\theta$, and the synthesis impedance Z are extracted and converted into a film thickness value in the impedance-type eddy current sensor. Measurement information on the film thickness of a metal film (Cu, Al, Au, or W), a barrier layer (Ta, TaN, Ti, TiN, or WN), or a polycrystalline silicon for a contact plug with a barrier layer can be obtained from the signal outputs X and Y, the phase $\theta$, the synthesis impedance Z, and the like. The measurement information can be used alone or in combination for detection of the polishing process, such as endpoint detection. The eddy current sensor can be provided within the polishing table near the surface of the polishing table so as to face a semiconductor wafer being polished via the polishing pad. With this arrangement, the eddy current sensor can detect the film thickness of the conductive film on the semiconductor wafer based on an eddy current flowing through the conductive film on the semiconductor wafer.

As can be seen from the equivalent circuit shown in FIG. 6, when each of voltage and current has a sine wave, the following relations (1) and (2) are established.

$$(R_1+j\omega L_1)I_1+j\omega MI_2=E \qquad (1)$$

$$(R_2+j\omega L_2)I_2+j\omega MI_1=0 \qquad (2)$$

From the above relations, the impedance z as viewed from a primary side appears as the equation (3).

$$z = \frac{E}{I_1} \qquad (3)$$

$$= \left[ \frac{E\left(Z_{11} - \frac{Z_M^2}{Z_{22}}\right)}{E} = Z_{11} - \frac{Z_M^2}{Z_{22}} = (R_1+j\omega L_1) - \frac{j^2\omega^2 M^2}{R_2+j\omega L_2} \right]$$

$$= R_1 + j\omega L_1 + \frac{\omega^2 M^2}{R_2+j\omega L_2} = x + jy$$

The resistance component x and the reactance component y appear as the following equations (4) and (5), respectively.

$$R_1 + \frac{\omega^2 M^2 R_2}{R_2^2 + \omega^2 L_2^2} = x \qquad (4)$$

$$\omega L_1 - \frac{\omega^3 M^2 L_2}{R_2^2 + \omega^2 L_2^2} = y \qquad (5)$$

Here, when $R_2$, which corresponds to a resistance of the eddy current, is eliminated from the equations (4) and (5), the following equation (6) is obtained.

$$(x-R_1)^2 + \left\{ y - \frac{\omega \times L_1(2+k^2)}{2} \right\}^2 = \left(\frac{1}{2}k^2\omega L_1\right)^2 \qquad (6)$$

Thus, the equation (6) represents a locus of a circular having a center of a point ($x=R_1$, $y=\omega L_1(2+k^2)/2$) and a radius of $k^2\omega L_1/2$, where k is a coupling coefficient, and $M=k(L_1 L_2)^{1/2}$.

Figure 12:
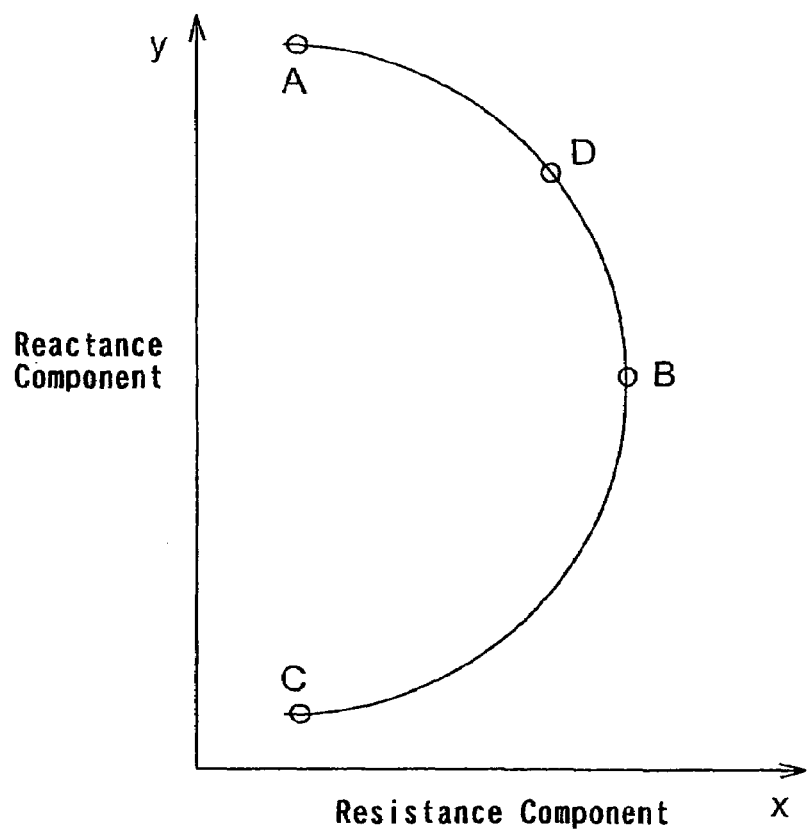
FIG. 12 is a graph showing a circular locus of a resistance component (R) and a reactance component (X) in an impedance coordinates according to change of the film thickness of a conductive film.

This means that an impedance z as viewed from the primary side is located at any point on a semicircle shown in FIG. 12. A resistance $R_2$, which corresponds to an eddy current loss, is represented by the following equation (7) where p is the volume resistivity, L is the equivalent length of the conductive film, W is the equivalent width of the conductive film, and d is the thickness of the conductive film.

$$R_2 = \rho \frac{L}{W \times d} \qquad (7)$$

FIG. 12 shows a locus of an impedance z as viewed from the AC signal source 124 in impedance coordinates. The vertical axis represents a reactance component (X), whereas the horizontal axis represents a resistance component (R). The point C represents a case in which the film thickness is as extremely large as 100 μm (the conductive film can be regarded as a perfect conductor). In this case, the impedance z as viewed from the terminals 128 and 130 of the AC signal source 124 (see FIG. 6) has an extremely increased eddy current in the conductive film 6 located near the sensor coil 100, an extremely reduced resistance component ($R_2$) connected equivalently in parallel to the sensor coil 100, and an extremely reduced reactance component. Accordingly, both of a resistance component (R) and a reactance component (X) become small.

When the conductive film becomes thin during polishing, an impedance z as viewed from the input terminals (terminals 128 and 130) of the sensor coil 100 has an increased equivalent resistance component ($R_2$) and an increased reactance component as compared to the point C. The point B represents a point at which an impedance z as viewed from the input terminals of the sensor coil 100 has a maximum resistance component (R). At the point B, an eddy current loss as viewed from the input terminals of the sensor coil 100 is maximized. When the conductive film becomes thinner during further polishing, an eddy current is reduced. Thus, a resistance component (R) as viewed from the sensor coil 100 is gradually reduced because an eddy current is gradually reduced. When the conductive film is completely removed by polishing, no more eddy current loss is caused. Accordingly, the resistance component ($R_2$) connected equivalently in parallel to the sensor coil 100 becomes infinite. Thus, only a resistance component ($R_1$) of the sensor coil 100 remains. At that time, a reactance component (X) corresponds to a reactance component ($L_1$) of the sensor coil itself. The point A represents this state.

When copper interconnections are formed in trenches formed in a silicon oxide film by a damascene process, a barrier layer such as tantalum nitride (TaN) or titanium nitride (TiN) is formed on the silicon oxide film, and a metal interconnection such as copper or tungsten having a high conductivity is further formed on the barrier layer. Accordingly, in a case of polishing such a conductive film, it is important to detect an endpoint of polishing the barrier layer. However, as described above, a barrier layer is formed as an ultrathin film having a relatively low conductivity and a thickness of an angstrom order, such as tantalum nitride (TaN) or titanium nitride (TiN).

With an eddy current sensor according to the present embodiment, it is possible to readily detect the film thickness of such a barrier layer near an endpoint of polishing. Specifically, the point D shown in FIG. 12 represents a case in which the film thickness is about 1000 Å. Variation of a resistance component becomes extremely large substantially in a linear manner according to changes of the film thickness from the point D to the point A at which the film thickness is zero. At that time, as shown in FIG. 12, a reactance component (X) has an extremely reduced amount of variation as compared to a resistance component (R). Accordingly, in an eddy current sensor employing a principle that the film thickness is detected based on variation of an oscillation frequency which is caused by changes of the reactance, the variation of the oscillation frequency is extremely smaller than changes of the film thickness, and hence it is necessary to raise the frequency in order to enhance a resolving power of the frequency variation.

An impedance-type eddy current sensor can detect changes of the film thickness with a fixed oscillation frequency by detecting variation of a resistance component. Thus, polishing conditions of an extremely thin film can clearly be monitored with a relatively low frequency. In the present embodiment, the film thickness is detected based on variation of a resistance component which is caused by changes of the film thickness. However, depending on the type of the conductive film, the film thickness may be detected based on variation of an oscillation frequency. Alternatively, the film thickness may be detected based on a synthesis impedance of a reactance component and a resistance component. Further, the film thickness may be detected by measuring the length of an arc, which is described later.

In order to detect a barrier layer having a relatively low conductivity, it is desirable to raise an oscillation frequency of the AC signal source 124 as compared to a case of detecting a metal film having a high conductivity. When an oscillation frequency is raised, it is possible to clearly monitor variation of the film thickness of the barrier layer in a range of 0 to 250 Å. In a case of a metal film having a relatively high conductivity, such as a copper film, it is possible to clearly detect changes of the film thickness even at a low oscillation frequency. Further, an oscillation frequency intermediate between the above frequencies may suitably be used for a tungsten film. Thus, it is desirable to select an oscillation frequency according to the type of a film to be measured.

Figure 13:
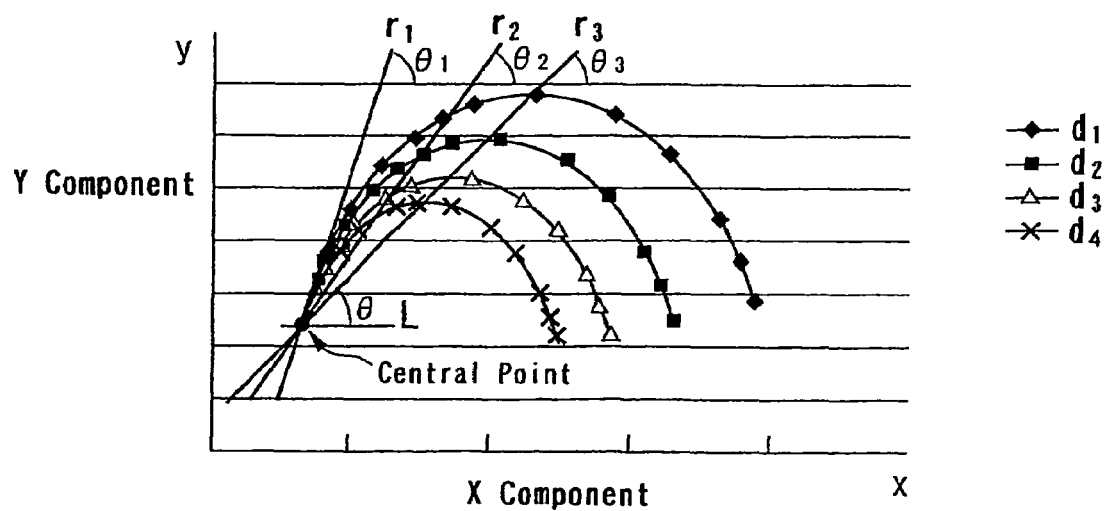
FIG. 13 is a graph showing variations of circular loci on the impedance coordinates according to variation of gaps between the conductive film and the sensor coil (the pad thickness)

Next, there will be described influence from the polishing pad 2 in the impedance-type eddy current sensor 10b. As shown in FIG. 1, the conductive film formed on a surface of the semiconductor wafer W being polished is measured via the polishing pad 2 by the sensor coil 100 of the eddy current sensor 10 embedded in the polishing table 1. In order to measure the film thickness of the conductive film 6 on the semiconductor wafer W being polished by the polishing pad 2 of the polishing apparatus, a gap G (see FIG. 5) formed between the upper end of the sensor coil 100 and the conductive film 6 varies according to the thickness of the polishing pad 2 interposed between the sensor coil 100 and the conductive film 6. As a result, as shown in FIG. 13, arc loci of X and Y components change according to gaps G formed by polishing pads having a thickness of $d_1$, $d_2$, $d_3$, and $d_4$ ($d_1 < d_2 < d_3 < d_4$). Thus, in order to accurately measure the film thickness of the conductive film 6 on the semiconductor wafer W based on the arc loci of the X and Y components, it is necessary to prepare measurement information on X and Y components of film thicknesses of the wafer with use of polishing pads having various thicknesses. Such measurement information may be prepared each time a polishing pad is replaced with a new one. After preparation of the measurement information, the film thickness of the conductive film 6 is measured.

In the measurement results of the X and Y components, as shown in FIG. 13, output values of the X and Y components of the same film thickness of the conductive film are connected by lines ($r_1, r_2, r_3$) with respect to the different gaps G between the upper end of the sensor coil and the conductive film. The lines ($r_1, r_2, r_3$) intersect each other at an intersection (central point) P. Thus, the central point P can be obtained from the measurement results of the X and Y components by the eddy current sensor. Each of these preliminary measurement lines $r_n$ (n=1, 2, 3 . . . ) is inclined at an elevation angle θ with respect to a base line L (horizontal line in FIG. 13) which passes through the intersection P and has a constant value of a Y component. The elevation angle θ depends on the film thickness of the conductive film.

Accordingly, even if the thickness of the polishing pad used for polishing the conductive film 6 of the semiconductor wafer W is unknown, the film thickness of the conductive film can be calculated based on correlation of variation tendency of elevation angles θ which has previously been measured according to the film thicknesses of the conductive film. Specifically, the central point P and a point having output values (measurement result) of X and Y components of the conductive film 6 are connected by an actual measurement line $r_n$. When an elevation angle θ of the actual measurement line $r_n$ with respect to the base line L is obtained, the film thickness of the conductive film 6 can be calculated based on the elevation angle θ. As a matter of course, the base line L may be a vertical line having a constant value of an X component in FIG. 13.

Next, there will be described a specific example of calculating the film thickness from an elevation angle θ. For example, polishing pads having different thicknesses and sample wafers having different film thicknesses of a copper film formed thereon are prepared. Points for combinations of these polishing pad and samples are measured in rectangular coordinates. For example, a point $(x_1, y_1)$ is calculated for the pad thickness of 2 mm and the film thickness of 2000 Å, and a point $(x_2, y_2)$ is calculated for the pad thickness of 3 mm and the film thickness of 2000 Å. Then, a line passing through these points is calculated. This line is represented by the following equation (8). The line has an elevation angle $\theta_1$ and passes through points for the common film thickness of 2000 Å.

$$y - y_1 = \frac{y_2 - y_1}{x_2 - x_1}(x - x_1) \qquad (8)$$

Similarly, a point $(x_3, y_3)$ is calculated for the pad thickness of 2 mm and the film thickness of 3000 Å, and a point $(x_4, y_4)$ is calculated for the pad thickness of 3 mm and the film thickness of 3000 Å. Then, a line passing through these points is calculated. This line is represented by the following equation (9). The line has an elevation angle $\theta_2$ and passes through points for the common film thickness of 3000 Å.

$$y - y_3 = \frac{y_4 - y_1}{x_4 - x_3}(x - x_3) \qquad (9)$$

These lines having different inclinations intersect at the central point P. When the elevation angles θ have the same value, the conductive films have the same film thicknesses irrespective of the pad thicknesses. The intersection (central point) of the lines having different inclinations is calculated by the following equations (10)-(13).

$$y = a_1 x + b_1 \qquad (10)$$

$$y = a_2 x + b_2 \qquad (11)$$

$$x = \frac{b_2 - b_1}{a_1 - a_2} \qquad (12)$$

$$y = \frac{a_1 b_2 - a_2 b_1}{a_1 - a_2} \qquad (13)$$

The controller 106 of the eddy current sensor is configured to measure the film thickness based on an elevation angle θ in the following manner. The controller 106 calculates a central point P corresponding to the type of the conductive film and elevation angles θ corresponding to the film thicknesses of the conductive film, and stores the central point P and the elevation angles θ in a storage device such as a memory. When the polishing apparatus is operated, the controller 106 calculates the film thickness of the conductive film based on an elevation angle θ of an actual measurement line $r_n$ which interconnects a point having output values of X and Y components and the central point P in the memory. Specifically, the controller 106 of the eddy current sensor forms an arithmetic unit so that the film thickness of the conductive film 6 on the semiconductor wafer W can quickly be measured during polishing. Information used to calculate a central point P and elevation angles θ may be stored in the memory, and a central point P and an elevation angles θ may be calculated at every measurement. Further, the central point may be calibrated by a calibration data table including the thicknesses and resistance components (Xm) and reactance components (Ym) corresponding to the film thicknesses.

Even if conductive films, which are to be measured by the eddy current sensor, are made of the same material, the conductive films have resistivities slightly varied according to deposition conditions such as a deposition apparatus or a deposition method. If the conductive films have different resistivities, output values of a resistance component (R) and a reactance component (X) vary according to their resistivities on a circular locus of those output values in FIG. 12. Specifically, when the resistivity has a small value with variation, the output values move clockwise on the circular locus. When the resistivity has a large value with variation, the output values move counterclockwise on the circular locus. Accordingly, a correction coefficient is preset according to variation of the resistivity which is caused by variation of deposition conditions. The measurement result by the eddy current sensor is calculated and corrected by the correction coefficient to cancel the variation of the resistivity. Thus, it is possible to accurately measure the film thicknesses of the conductive films.

For the above purposes, the controller 106 (see FIG. 1) of the eddy current sensor is configured to cancel the variation of the resistivity. Specifically, a correction coefficient to cancel variation of the resistivities of conductive films which is caused by variation of deposition conditions is previously obtained and stored in a storage device such as a memory. When the film thickness of a conductive film is measured, processes such as multiplication of output values of X and Y components by the correction coefficient in the memory are conducted so as to measure the film thickness of the conductive film with high accuracy. Thus, the controller 106 of the eddy current sensor can measure the film thickness of a conductive film 6 on a semiconductor wafer W with high accuracy without any error caused by variation of deposition conditions.

When a barrier layer (e.g., a TaN film having a thickness of about 30 nm) is polished, measurement points may not form a circular shape while they move on an impedance plane. Even in such a case, variation of the film thickness and values of the film thickness can be obtained by enlarging a portion of the impedance plane and measuring a movement distance of measurement points.

When a copper layer as a conductive film of a semiconductor wafer is polished but a TaN layer (barrier layer) having an extremely small thickness remains on the semiconductor wafer, an eddy current produced in a silicon material of the semiconductor wafer may largely affect measurement results of X and Y components by the eddy current sensor. Accordingly, in order to accurately measure the film thickness of a ultrathin barrier layer such as a remaining TaN layer without influence from a silicon material of the semiconductor wafer, it is necessary to remove X and Y components due to the silicon material from the measurement results so as to extract only coordinate variation due to the barrier layer such as a TaN layer. Specifically, X and Y components due to the silicon material in the semiconductor wafer having no conductive films deposited thereon are previously measured by the eddy current sensor. The X and Y components due to the silicon material are removed from the measurement results of the eddy current sensor. Thus, even in a case of a barrier layer such as a TaN layer remaining on a semiconductor wafer, the film thickness of the barrier layer can be measured with high accuracy. Specifically, influence from a silicon material which does not change during polishing can be removed, and variation by changes of the film thickness of the barrier layer can be displayed in an enlarged state on an impedance plane during polishing.

Accordingly, in the present embodiment, X and Y components of a silicon substrate having no conductive films are previously measured. The controller 106 (see FIG. 1) of the eddy current sensor performs phase rotation to conform output values of the X and Y components to the x-axis or the y-axis in the xy-coordinates. For this purpose, a rotational angle θ to perform the above phase rotation is calculated in the xy-coordinates (rectangular coordinates) and stored in a storage device such as a memory.

For example, when a barrier layer such as a TaN layer remaining on a semiconductor wafer (silicon substrate) is measured, a locus shown by a solid line in FIG. 14A is obtained. A dashed line represents X and Y components of a silicon substrate. As shown in FIG. 14A, changes of the film thickness of the barrier layer (TaN) are extremely small. In this case, coordinates of a point P which is influenced by the silicon substrate are inputted into the controller 106 having a conversion logic software so as to perform rotational movement of coordinate axes. Specifically, as shown in FIG. 14B, rotation is performed so as to conform an impedance components of the silicon substrate to the x-axis or y-axis. Then, as shown in FIG. 14C, only components of TaN are enlarged in the x-direction or y-direction. Thus, it is possible to avoid influence from the impedance components of the silicon substrate and improve the detection sensitivity. According to the above method, influence from the impedance components of the silicon substrate can be cancelled without previous measurement of X and Y components of the silicon substrate, and only variation of the impedance of the barrier layer can be displayed in an enlarged manner.

Specifically, phase rotation and offset adjustment (parallel displacement) are performed at first; and then coordinate systems are converted as shown in FIG. 14B. Thus, X and Y components of the silicon substrate can be cancelled by rotation of a phase angle. Next, as shown in FIG. 14C, expansion is performed in the y-direction so as to display only components of the barrier layer in an enlarged manner, so that the film thickness of the barrier layer can be detected with high accuracy. Thus, this method employs phase rotation and expansion to measure the film thickness of a conductive film on a substrate.

More specifically, the controller 106 of the eddy current sensor serves to cancel coordinate components influenced from the silicon and to expand coordinate components corresponding to the film thickness of the conductive film 6 such as an ultrathin barrier layer so as to accurately measure the film thickness of the conductive film. In this example, phase rotation is performed on results from the eddy current sensor. However, only the sensitivity of a barrier layer may be extracted and outputted by subtracting X or Y components of results including only silicon from results including the barrier layer.

Further, with respect to a distance from the sensor coil 100 to the semiconductor wafer (conductive film), if a conductive material such as a stainless metal material in the top ring 3 holding the semiconductor wafer is located near the sensor coil 100, X and Y components due to the conductive material of the top ring 3 may affect output values. Accordingly, it is desirable that a conductive material such as a stainless metal material in the top ring 3 holding the semiconductor wafer is positioned distant from the sensor coil 100 so that the top ring 3 does not affect output values of X and Y components from the eddy current sensor (eddy current produced in the conductive film of the semiconductor wafer). Preferably, the conductive material may be positioned at least 10 mm distant from the sensor coil 100. In this case, influence from a stainless metal material in the top ring 3 can be reduced substantially to a negligible level. When the conductive material in the top ring has an influence, the aforementioned phase rotation can reduce the influence to a negligible level.

Calibration in the eddy current sensor may be performed as follows. A conductive film of a reference wafer is polished, and the film thickness of the reference wafer is measured. The phase, the gain, and the offset of the main amplifier 104 are adjusted, and inversion is performed in the main amplifier 104 so that a base point, at which measurement starts, and an endpoint, at which the conductive film is removed, of a circular locus of resistance components (R) and reactance components (X) in FIG. 12 are constant. Thus, it is possible to eliminate influence by individual differences of the eddy current sensor and accurately detect changes of the film thickness of the conductive film.

The controller 106 of the eddy current sensor can quickly perform film thickness measurement of a conductive film during polishing. If a polishing mode is required to be switched at a predetermined film thickness, the preamplifier or the main amplifier may previously be configured in a range such that the film thickness can be measured in an angstrom order so as to perform accurate film thickness measurement. For example, in a case where a polishing mode is switched at about 300 Å, the preamplifier or the main amplifier may be configured so that measurement results are over the measurable range (i.e., in saturation) when a Cu layer or a W layer having a thickness of at least about 300 Å is polished. The preamplifier or the main amplifier may be configured to have a linear amplification degree when the Cu layer or the W layer has a thickness less than about 300 Å.

Figure 15A:
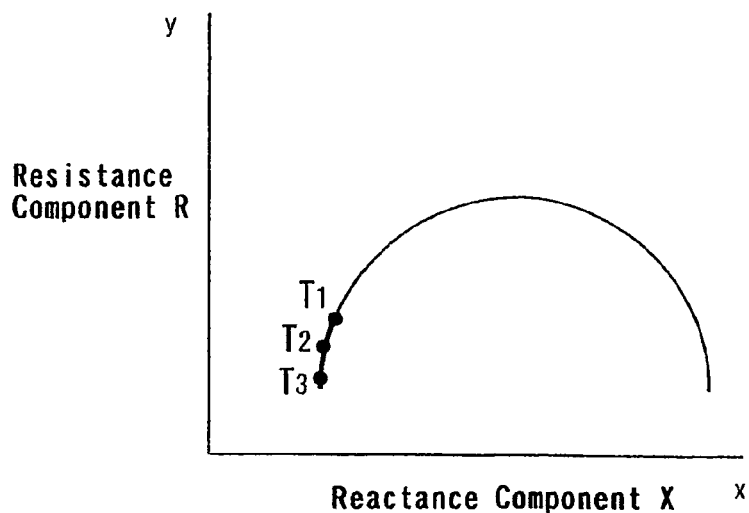
FIGS. 15A through 15D are graphs showing a method of setting a gain of an amplifier suitable for film thickness detection.
Figure 15B:
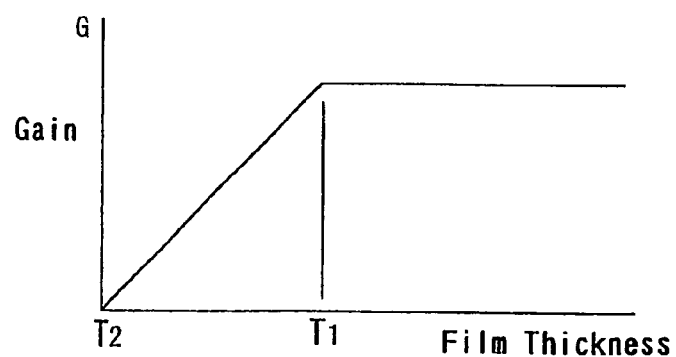
Figure 15C:
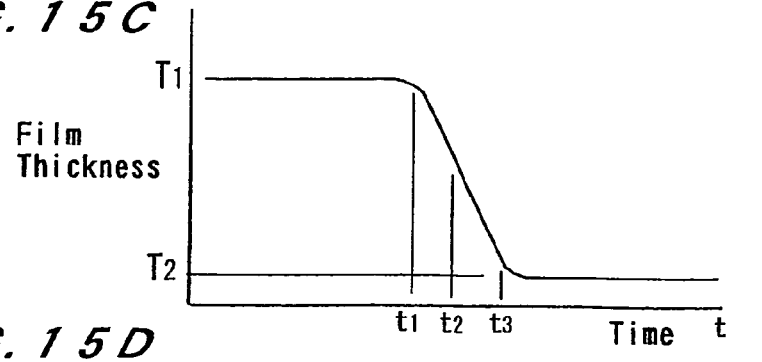
Figure 15D:
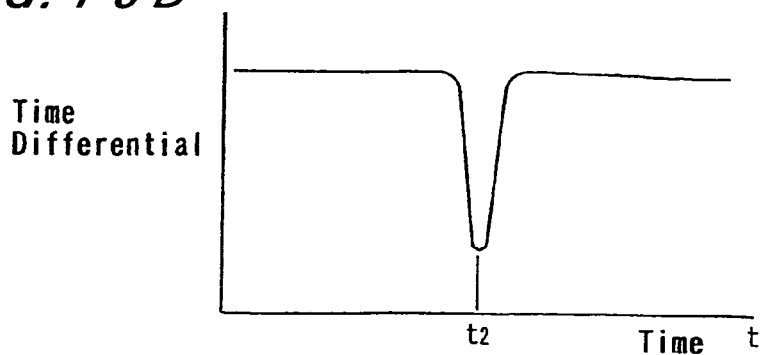

Specifically, the preamplifier or the main amplifier may be configured to have characteristics such that signals are saturated above a predetermined film thickness and changed below the predetermined film thickness. Thus, a process can be switched at the predetermined film thickness. At that time, a polishing profile has a steep shape, and setting can be facilitated because of a widened width of setting of differential values. For example, when a polishing process is switched at a predetermined film thickness $T_1$ as shown in FIG. 15A, a gain of an amplifier is previously set to be saturated at the film thickness $T_1$ as shown in FIG. 15B. Thus, as shown in FIG. 15C, substantially constant outputs can be obtained below the film thickness $T_1$. Outputs begin to be lowered dramatically at the film thickness $T_1$. As shown in FIG. 15D, $t_2$ is be detected at a bottom of a time differential, so that the predetermined film thickness $T_1$ can clearly be detected during polishing.

Based on the measurement results described above, the controller 106 of the eddy current sensor switches an operation mode from the film thickness measurement described above into film thickness measurement for a barrier layer which employs phase rotation and expansion. Thus, it is possible to perform a polishing process having high accuracy. In this operation mode, the presence of a barrier layer having a small film thickness can reliably be detected by switching an oscillation frequency or an amplification degree, so that an endpoint of the polishing process can properly be determined. Further, in a case where a tungsten film, a copper film, or the like is polished, it is possible to prevent dishing or erosion during polishing by switching a polishing process from a high-pressure polishing process into a low-pressure polishing process at a predetermined film thickness.

In a case of a substrate having a low resistance (e.g., a resistivity of 0.01 to 0.03 Ω·cm), e.g., a tungsten process or the like, the precision of the film thickness measurement is lowered because of variation of the resistance of the substrate. If the resistivity and the film thickness of a metal film formed on a substrate are the same, the length of an arc in a curve of a locus in an impedance coordinates is constant irrespective of the resistance of the substrate. For example, movement (movement distance) of measurement points is previously measured on an impedance curve according to the resistance of a substrate for calibration, the thickness of the metal film, and the change of the film thickness. Next, the film thickness of an actual substrate can be calculated based on a distance between a polishing start point, which is obtained when the substrate is polished, and the present point in an arc on an impedance curve. It is desirable that the metal material of the substrate for calibration is the same material as a conductive material of the actual substrate. Specifically, even if a substrate has a low resistivity or is formed by an unstable material, changes of the film thickness of the conductive film can properly be calculated by previous calculation of film thicknesses of various kinds of metals and positions of measurement points in an arc.

There will be described a method using the length of an arc, which is suitable in film thickness measurement for a film having a relatively low conductivity, such as a W film, in a case of a substrate having a low resistance. A locus on an impedance plane is calculated from x, y, and z of polishing data and can be employed for endpoint detection of a polishing process. However, if absolute values in coordinate axes are used as signals for endpoint detection, then high sensitivity cannot be achieved because measurement points vary in respective polishing processes due to influence of an underlying-silicon substrate. From this point of view, the length of a polishing locus from coordinates $(X_0, Y_0)$ at a polishing start point (t=0) to coordinates locus $(X_p, Y_p)$ after a polishing time t is measured. The endpoint of the polishing can be detected based on changes of the length of the polishing locus. Since this method employs measurement of the arc length, absolute values of changes from the polishing start point can always be obtained even if a polishing locus moves on the impedance plane. Accordingly, it is possible to enhance the measurement sensitivity.

Figure 16A:
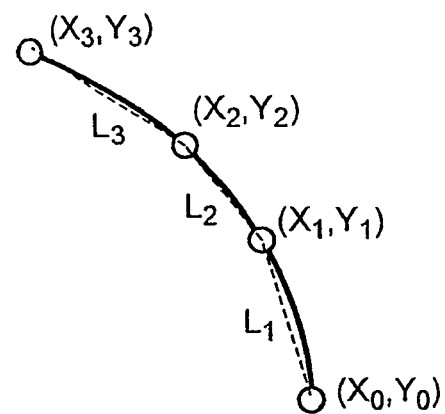
FIGS. 16A and 16B are diagrams showing a method of measuring the film thickness based on the length of arcs.
Figure 16B:
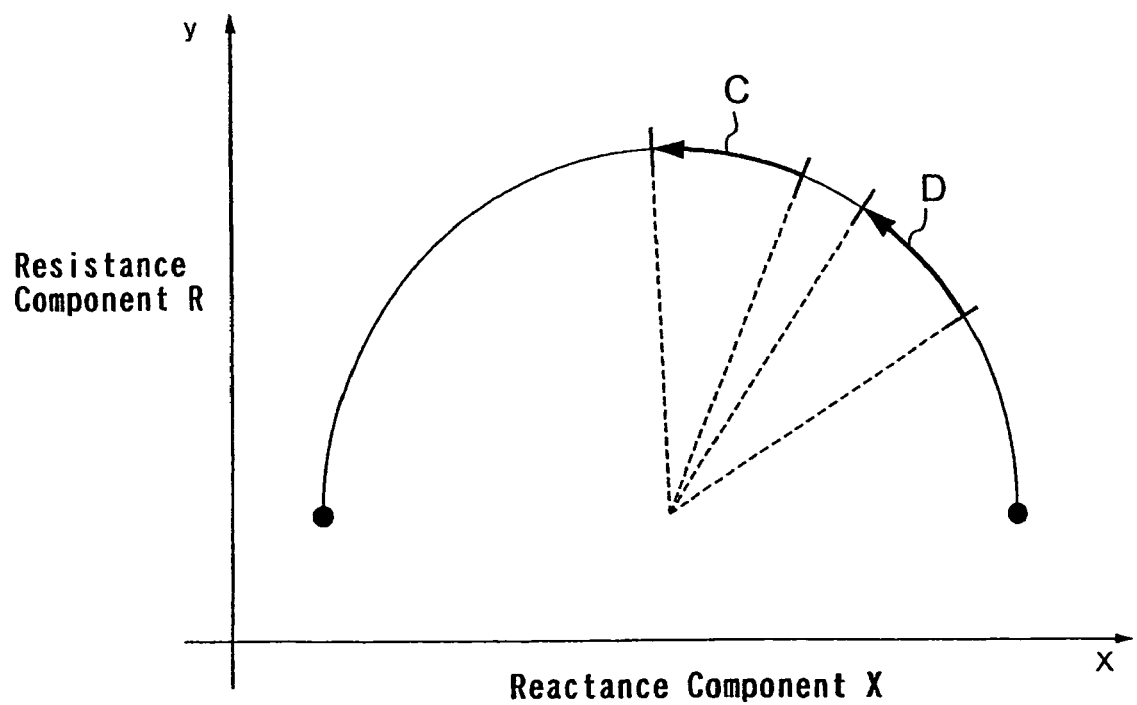

FIGS. 16A and 16B show an example of the method employing measurement of the arc length. FIG. 16A illustrates the arc length on the impedance plane, and FIG. 16B illustrates the arc lengths C and D when underlying silicon substrates have different conductivities. For example, when the polishing table is rotated at a rotational speed of 60 min$^{-1}$, the sensor coil passes through a predetermined area of a substrate each rotation, i.e., each one second, and obtains data on the predetermined area. Thus, coordinates $(X_0, Y_0)$ at t=0, coordinates $(X_1, Y_1)$ at $t_1$, and coordinates $(X_2, Y_2)$ at $t_2$ are obtained. Based on these data, the length $L_1$ of an arc between the point at t=0 and the point at t=$t_1$ is obtained. Similarly, the length $L_2$ of an arc from $t_1$ to $t_2$ is obtained, and the length $L_3$ of an arc from $t_2$ to $t_3$ is obtained.

There will be described measurement of the film thickness of a tungsten film in a case where low-resistance substrates having different resistivities are used as the silicon substrate. In such a case, if the silicon substrates have the same resistivity, the impedance locus is in the form of an arc on an impedance plane during polishing. Even though the low-resistance substrates having different resistivities are used as the silicon substrate, the impedance loci are on the same arc of the same length when the film thicknesses of the W film have the same variation amount.

For example, as shown in FIG. 16B, when a W film having a thickness of 3000 Å is polished, an arc C in which the underlying silicon substrate has a resistivity of 0.03 Ω·cm has the same length as an arc D in which the underlying silicon substrate has a resistivity of 0.01 Ω·cm. There is a difference between rotation angles as seen from a center of a semicircle on the impedance coordinates because of influence from the resistivities of the underlying silicon substrates. Accordingly, the difference between the rotation angles is calibrated from calibration data on substrates having known resistivities as described above. Thus, it is possible to calculate the film thickness of the W film formed on the substrate including an underlying silicon substrate having an unknown resistivity.

According to a polishing apparatus having an eddy current sensor as described above, film thickness measurement can be performed over the entire surface of a semiconductor wafer at short intervals to detect an endpoint of a polishing process. Further, since an endpoint can be detected for a barrier layer such as Ta, TaN, TiN, or Ti, it is possible to detect an endpoint of a polishing process with extremely high accuracy. At that time, even if a patch residue (local residue) of a conductive film is produced at the last stage of the polishing process, the eddy current sensor according to the present invention can detect the patch residue having a diameter of at least 5 mm. Thus, it is possible to reliably polish and remove the patch residue during the polishing process. Furthermore, even in a case where a semiconductor wafer has multilayer interconnections made of a conductive material, the eddy current sensor can reliably detect a conductive film as long as the density of the interconnections is not more than 90%.

It is desirable to set cut-off frequencies of various filters including a LPF, a BPF, a HPF, and a notch filter so as to analyze noise components by signal regeneration and remove the noise components after measuring a torque current of a polishing table, a change of the impedance of a metal film by an eddy current, a change of the film thickness of an oxide film by an optical monitor, a change of the film thickness signal of a metal film or an oxide film by microwaves, and the like. For example, when a cut-off frequency of a LPF in the eddy current sensor is set in a range of 0.1 to 1 kHz, noise components caused in the sensor can be removed so that characteristic points can accurately be detected by accurate signal detection.

For example, when a metal film is removed by electrolytic polishing or chemical mechanical polishing, a pressing force of the top ring against the polishing pad, a temperature of the polishing table, rotational speeds of the polishing table and the top ring, and the like may be controlled with a closed loop control based on an absolute film thickness measured by the eddy current sensor in order to control a polishing rate and a within wafer uniformity in the polishing process.

Further, the eddy current sensor may be used for polishing prediction or preventive maintenance. For example, the impedance properties of the eddy current sensor which are obtained from a wafer being polished are measured every predetermined time. Based on a correlation between the impedance properties and model data, polishing prediction is performed so as to predict a remaining time required to obtain the impedance properties corresponding to the model data of the endpoint of the polishing process. Thus, irrespective of rotation of the polishing table in the CMP apparatus, it is possible to detect a polishing endpoint at intervals shorter than a period of time required to make one revolution of the polishing table. Further, it is possible to predict a remaining time until the polishing endpoint at an early stage. Accordingly, since the progress of the polishing process can be checked, it is possible to promptly cope with an anomaly caused during polishing.

It is also possible to detect an endpoint of a process for processing slurry used for polishing or waste liquid by impedance analysis with an eddy current sensor according to the present invention. For example, electromagnetic waves having a frequency of 2, 8, 20, and 160 MHz, and a microwave having a frequency of 30 to 300 GHz are applied to slurry on the polishing pad, slurry in a slurry discharge line which has been discharged during the polishing process, or slurry in a slurry discharge tank. The demagnetizing field, the reflection amplitude, and the impedance variation of the reflection are detected. Then, a standard impedance before the polishing, relative values, and absolute values are averaged. Thus, it is possible to detect a polishing endpoint from variation of time differentials of the averaged values. Further, in a deposition process such as electrolytic plating or electroless plating, or a polishing process such as (ultrapure water) electrolytic polishing or electrochemical polishing, changes of the impedance of waste liquid of a plating solution, an electrolyte, ultrapure water, or the like may continuously be monitored to detect an endpoint of the deposition process or the polishing process.

Furthermore, it is possible to determined anomaly by an integral process of signals. Specifically, an integral value of the impedance of the eddy current sensor or the microwave sensor is equal to a time integral value of the impedance of the sensor from the polishing start point. Impedances T(x), T(y), and T(z) and the film thickness detected by the sensor are integrated from the polishing start time $t_0$ to the present time t to calculate a signal integral value St(f). Specifically, the signal integral value St(f) is calculated from the polishing start time to the present time. A ratio of the signal integral value St(f) to a signal integral value So(f) which has previously been calculated from a polishing start time to a polishing endpoint of a reference wafer is calculated. The ratio can be used to detect a polishing endpoint or anomaly of polishing conditions.

In a method of detecting a polishing (process) endpoint at which a conductive film is removed from a wafer, an edge cutting process may be performed in an eddy current sensor or a microwave sensor. Specifically, a semiconductor wafer is divided into a plurality of zones (N zones), e.g., five zones. In an eddy current sensor, X and Y components of the impedance, a phase θ, a synthesis impedance Z, a frequency F, and a film thickness value converted therefrom are obtained for each zone. In a microwave sensor, a reflection signal and a transmission signal are obtained for each zone. A polishing (process) endpoint is detected when a value (determination value) obtained from data on the respective zones is higher than a predetermined value or lower than a predetermined value. For example, such endpoint detection may employ a determination value including a single value of the data on an optimum zone, an average value of the data on all N zones, an average value of the data on a desired combination of N zones, an effective value, a first time-derivative of the data, a second time-derivative of the data, and a nth time-derivative of the data.

Further, in order to detect an endpoint, at which a metal film is completely removed, based on a reference time, which is calculated from sensor signals, an arithmetical operation is performed on the reference time with a coefficient to calculate an additional period of polishing time. The additional period of polishing time is added to the reference time to obtain the polishing endpoint. Thus, it is possible to properly set a polishing endpoint.

Figure 17:
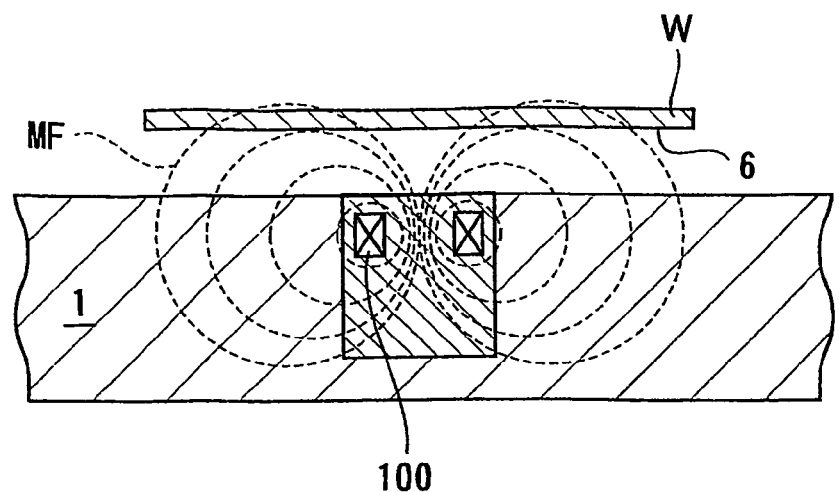
FIG. 17 is a cross-sectional view showing a magnetic flux distribution by an eddy current sensor when the eddy current sensor is embedded in a polishing table made of an insulating material.

For example, as shown in FIG. 17, when the sensor coil 100 is disposed within the polishing table 1 made of ceramics (insulating material) such as SiC, a magnetic flux MF is produced by the sensor coil 100 so as to form large paths (magnetic circuits) in a detection space, which is located above the polishing table 1. Thus, an eddy current can effectively be produced in a conductive film 6 on a semiconductor wafer W to be polished by the polishing pad (polishing surface) on the polishing table 1.

Figure 18:
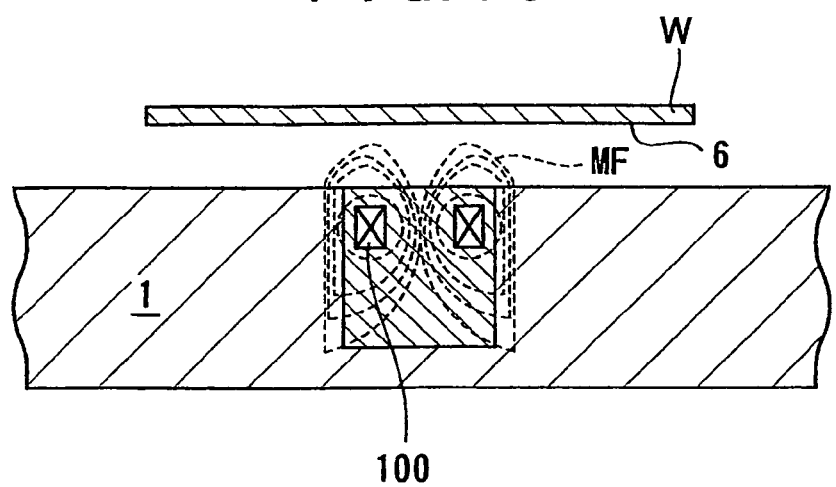
FIG. 18 is a cross-sectional view showing a magnetic flux distribution by an eddy current sensor when the eddy current sensor is embedded in a polishing table made of a conductive material.

However, as shown in FIG. 18, if a sensor coil 100 of an eddy current sensor is embedded in a polishing table 1 made of a conductive material such as stainless, then, a magnetic flux MF by the sensor coil 100 produces an eddy current in the polishing table 1 so as to lower the strength of a magnetic flux emitted externally. In such a case, since a magnetic flux MF that reaches a semiconductor wafer W is lessened, signals of an eddy current produced in the conductive film are weakened. Accordingly, the eddy current produced in the conductive film cannot be detected, or otherwise the sensor coil 100 is required to have an extremely high sensitivity.

Accordingly, it is not desirable to locate a conductive material other than a conductive material to measured near the sensor coil of the eddy current sensor (in an installation environment). However, for example, a stainless material may be suitable for a material of the polishing table, in which the sensor coil is embedded. Specifically, although ceramic materials such as SiC or alumina ($Al_2O_3$), which has a high thermal conductivity, have widely been used as a material for the polishing table, a stainless material can reduce manufacturing cost. When SiC is used as a material for the polishing table, the temperature of the polishing table is generally controlled by cooling water flowing through the polishing table. For example, an oxide film is unlikely to be influenced by the temperature. Accordingly, when the oxide film is polished, a stainless material can be used as a material for the polishing table without temperature control.

However, a stainless material is conductive. When the eddy current sensor forms an alternating magnetic field, an eddy current is produced within the stainless material so that a magnetic flux emitted to a conductive film on a semiconductor wafer W is adversely lessened. In such a case, it is desirable that a magnetic flux to produce an eddy current in a conductive film to be measured is less influenced by the installation environment of the sensor coil. Specifically, even if the installation environment of the sensor coil includes a conductive material such as a stainless material, the eddy current sensor should preferably have a high sensitivity.

Figure 19:
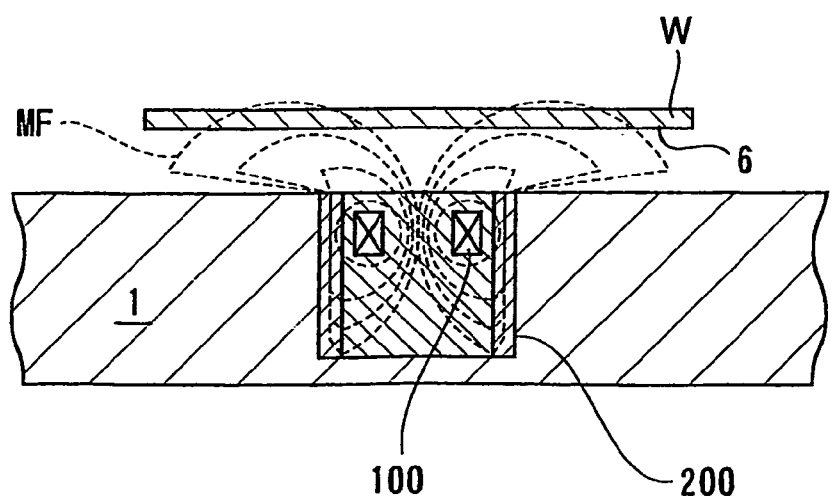
FIG. 19 is a cross-sectional view showing a magnetic flux distribution by an eddy current sensor according to a second embodiment of the present invention.

FIG. 19 shows a sensor coil 100 according to a second embodiment of the present invention. The sensor coil 100 is housed in a cylindrical housing 200 made of a material having a high magnetic permeability. As described above, when the polishing apparatus polishes the conductive film 6 of the semiconductor wafer W by the polishing pad, the sensor coil 100 is disposed in the polishing table 1 made of a conductive material such as a stainless material so as to measure the film thickness of the conductive film 6.

The housing 200 is made of a material having a high magnetic permeability, such as ferrite, amorphous material, permalloy, super-permalloy, or Mumetal. For example, the relative permeability μ of the housing 200 is 50. Thus, the housing 200 can pass a magnetic flux therethrough 50 times as much as air present around the sensor coil. In other words, the housing 200 can pass an equivalent magnetic flux with one-fiftieth thickness of an electrically insulating material such as a ceramic material disposed around the sensor coil 100.

With the arrangement shown in FIG. 19, a current is supplied to an air-core coil of the sensor coil 100 housed in the housing 200 to produce a magnetic flux MF. As shown in FIG. 19, even when the polishing table 1 is made of a conductive material such as a stainless (SUS) material, an eddy current is not produced in the polishing table 1 by the magnetic flux MF. Thus, paths (magnetic circuits) of the magnetic flux MF, which are required for measurement, are not reduced, unlike an example shown in FIG. 18. Accordingly, it is possible to maintain paths (magnetic circuits) of the magnetic flux MF so as to effectively produce an eddy current in the conductive film 6 of the semiconductor wafer W. Specifically, the housing 200 serves as a path to prevent the magnetic flux MF produced by the air-core coil of the sensor coil 100 from passing through the polishing table 1 of a conductive material and to expand the magnetic flux MF into the detection space on the semiconductor wafer W. Thus, the magnetic flux MF can produce a large amount of an eddy current in the conductive film 6 to be measured.

Figure 20:
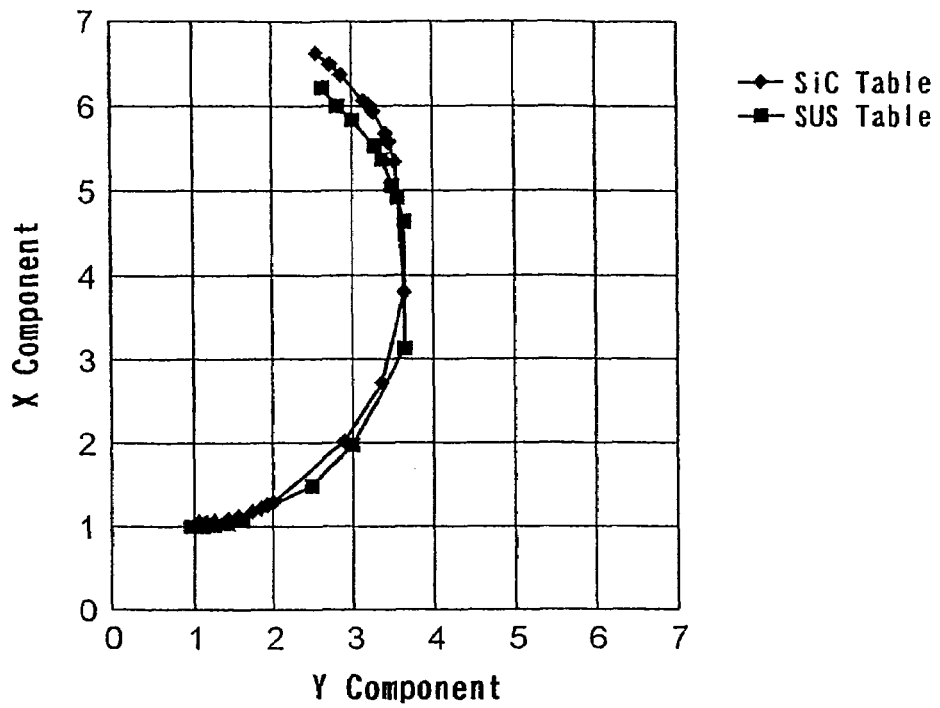
FIG. 20 is a graph showing characteristics of an eddy current sensor according to the second embodiment in a case where the eddy current sensor is embedded in a polishing table made of a conductive material (SUS) and in a case where the eddy current sensor is embedded in a polishing table made of an insulating material (SiC)

For example, in FIG. 20, boxes represent a case in which the polishing table 1 is made of a conductive material such as a stainless (SUS) material, whereas diamonds represent a case in which the polishing table 1 is made of a ceramics material (insulating material) such as SiC. As shown in FIG. 20, even in the case of the polishing table 1 made of a conductive material, it is possible to maintain substantially the same sensitivity as in the case of the polishing table 1 made of a ceramics material. Specifically, it is possible to obtain the measurement sensitivities such that output values of X and Y components change on similar circular loci in rectangular coordinates as viewed from the sensor coil. The impedance is represented by complex numbers including a resistance component and a reactance component. The impedance as viewed from the sensor coil is detected as X components which are output values of cosine synchronous detection and Y components which are output values of sine synchronous detection. X components correspond to the resistance components, and Y components correspond to the reactance components.

Figure 21:
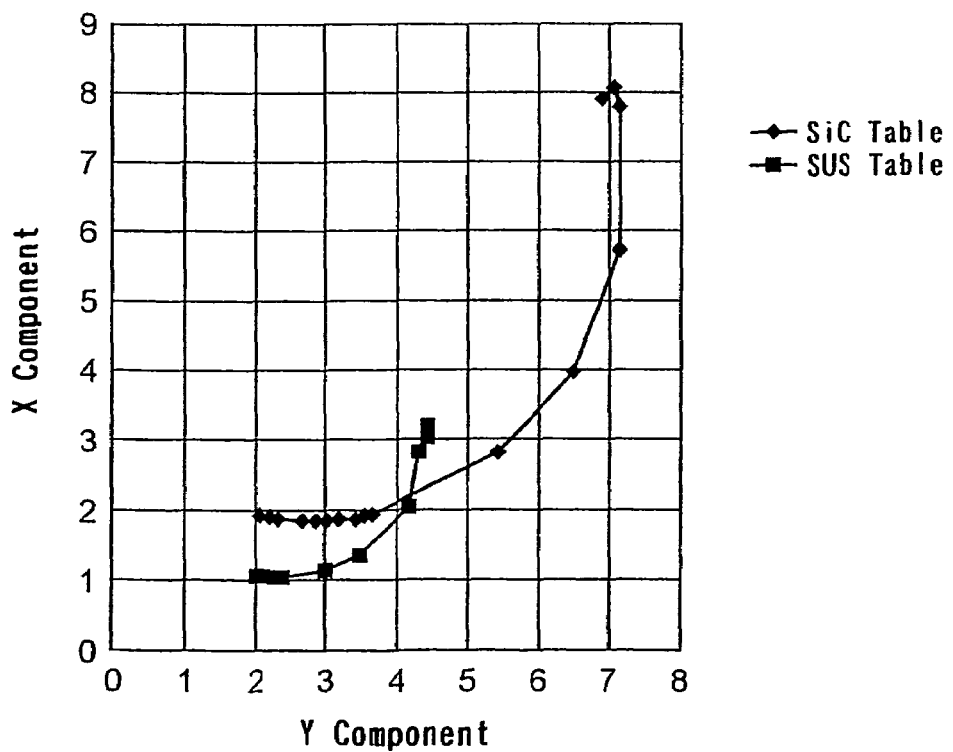
FIG. 21 is a graph showing characteristics of an eddy current sensor in a case where the eddy current sensor is embedded in a polishing table made of a conductive material (SUS) and in a case where the eddy current sensor is embedded in a polishing table made of an insulating material (SiC)

FIG. 21 shows a comparative graph of the sensor sensitivities of the eddy current sensor shown in FIG. 18 and the eddy current sensor shown in FIG. 17. Specifically, diamonds represent a case of the polishing table 1 made of a ceramics material (insulating material) such as SiC shown in FIG. 17, whereas boxes represent a case of the polishing table 1 made of a conductive material such as a stainless (SUS) material shown in FIG. 18. As can be seen from FIG. 21, a sufficient amount of eddy current is produced in the conductive film by a sufficient amount of magnetic flux in the case shown in FIG. 17. On the other hand, a sufficient amount of eddy current is not produced in the conductive film because of an insufficient amount of magnetic flux. In the eddy current sensor according to the present embodiment, since the sensor coil 100 is housed in the cylindrical housing 200 having a high magnetic permeability, it is possible to achieve a magnetic flux distribution as shown in FIG. 19. Thus, even when the polishing table is made of a conductive material such as a stainless (SUS) material, the eddy current sensor can have substantially the same sensitivity as in the case of the polishing table made of a ceramic material (insulating material) such as SiC or alumina ($Al_2O_3$). Such a material having a high magnetic permeability includes ferrite, amorphous material, permalloy, super-permalloy, and Mumetal.

Thus, as shown in FIGS. 20 and 21, even when the polishing table 1 is made of a conductive material such as a stainless material for a design purpose, the eddy current sensor according to the present embodiment can prevent lowered output values of X and Y components and a largely lowered sensitivity as compared to the case of the polishing table made of a ceramic material such as SiC.

In the present embodiment, the sensor coil 100 is housed in the cylindrical housing 200 having a high magnetic permeability, and the housing 200 is embedded in the polishing table 1. However, as shown in FIG. 22, a ceramic material (insulating member) 200a such as SiC may be embedded within a range of paths of a magnetic flux MF to produce an effective eddy current in a conductive film 6 of a semiconductor wafer W. In this case, the magnetic flux MF produced by an air-core coil of the sensor coil 100 does not produce an eddy current uselessly in the polishing table 1 made of a conductive material such as a stainless material. Thus, it is possible to produce a large amount of eddy current in the conductive film 6 to be measured. This configuration has less design limitation than a case in which the entire polishing table is made of a ceramic material in view of cost or the like.

In the above embodiments, the conductive film formed on the semiconductor wafer is polished by the polishing pad attached on the polishing table. However, the present invention is applicable to a process control using film thickness measurement of a conductive film in an etching process, an electrolytic polishing process, an electrochemical polishing process, and an ultrapure water electrolytic process. Further, the process control using film thickness measurement of a conductive film may be employed not only for removal of the conductive film, but also for deposition of the conductive film.

Figure 23:
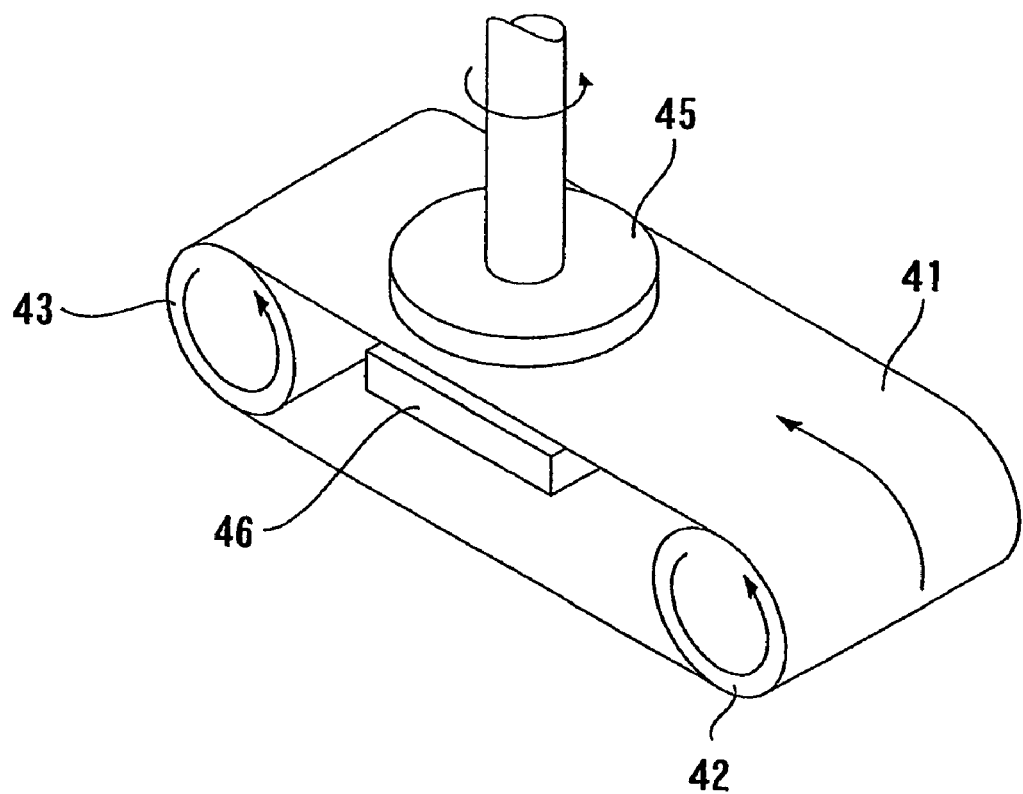
FIG. 23 is a perspective view showing a polishing apparatus according to another embodiment of the present invention.

FIG. 23 shows a polishing apparatus according to another embodiment of the present invention. The polishing apparatus shown in FIG. 23 has a polishing pad 41 in the form of a belt, rollers 42 and 43 to rotate the polishing pad 41, and a top ring (holding device) 45 for rotating a semiconductor and pressing the a semiconductor wafer against the polishing pad 41. A surface of the semiconductor wafer is brought into sliding contact with the polishing pad 41 (polishing surface). Thus, the surface of the semiconductor wafer is polished. The polishing apparatus has a support 46 located right below the top ring 45. An eddy current sensor according to the present invention is embedded in the support 46 to monitor conditions of the surface of the semiconductor wafer.

Figure 24:
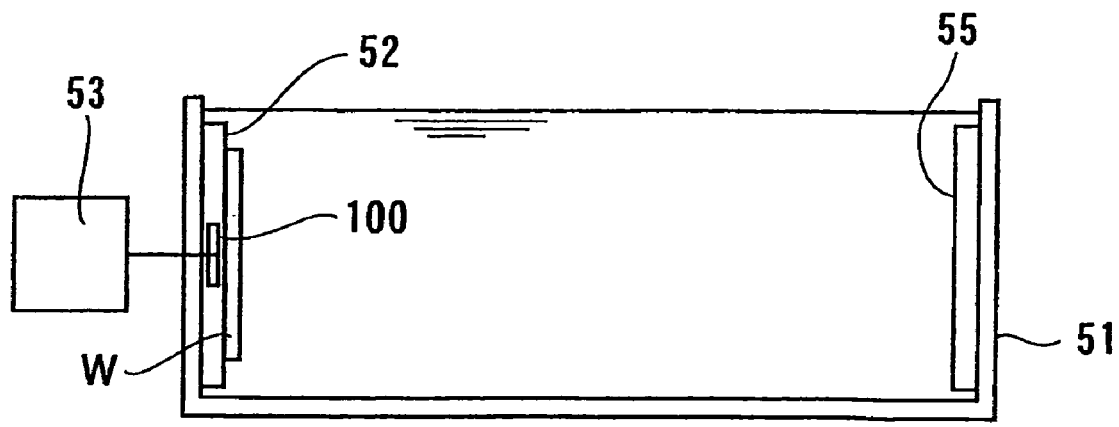
FIG. 24 is a schematic view showing a deposition apparatus having an eddy current sensor according to the present invention.

Further, an eddy current sensor according to the present invention can be used not only in a polishing apparatus, but also in various substrate processing apparatuses. For example, a plating apparatus for plating a film on a surface of a substrate may include an eddy current sensor according to the present invention. FIG. 24 shows an example of a plating apparatus having an eddy current sensor according to the present invention. The plating apparatus serves to deposit a metal plated film on a semiconductor wafer W and has a plating tank 51 holding a plating solution therein, a holder 52 for holding the semiconductor wafer W in the plating tank 51, and an anode 55 disposed so as to face the semiconductor wafer W. A sensor coil 100 of the eddy current sensor is provided within the holder 52 and connected to a controller 53. The controller 53 includes an AC signal source and a synchronous detection circuit to detect the film thickness of the metal plated film deposited on the semiconductor wafer W. Thus, the conditions of deposition of the plated film can reliably be obtained in a non-contact manner.

The present invention is not limited to the above embodiments. For example, the substrate holding device in the polishing apparatus and the eddy current sensor are not limited to the illustrated examples. Although certain preferred embodiments of the present invention have been shown and described in detail, it should be understood that various changes and modifications may be made therein without departing from the scope of the appended claims.

INDUSTRIAL APPLICABILITY

The present invention is suitable for use in an eddy current sensor suitable for detecting the thickness of a conductive film formed on a surface of a substrate such as a semiconductor wafer.

The invention claimed is:

1. An eddy current sensor comprising:
    a sensor coil disposed near a conductive film formed on a substrate;
    a signal source configured to supply an AC signal to said sensor coil to produce an eddy current in the conductive film;
    a detection circuit operable to detect the eddy current produced in the conductive film based on an impedance as viewed from said sensor coil; and
    a controller configured to specify a point including a resistance component and a reactance component of the impedance in rectangular coordinates and to detect a film thickness of the conductive film from an angle formed by a base line and a line connected between the point and a predetermined central point in the rectangular coordinates, wherein the base line is parallel to either a reactive component axis of the rectangular coordinates or a resistive component axis of the rectangular coordinates.

2. The eddy current sensor as recited in claim 1, wherein said controller is configured to detect the film thickness of the conductive film from the angle without influence due to a distance between said sensor coil and the conductive film.

3. The eddy current sensor as recited in claim 1, wherein the predetermined central point is calibrated by a calibration data table including film thicknesses and resistance components (Xm) and reactance components (Ym) corresponding to the film thicknesses.

4. A substrate processing apparatus comprising:
    a processing device configured to process the substrate; and
    the eddy current sensor as recited in claim 1.

5. A polishing apparatus comprising:
    a polishing surface;
    a substrate holding device configured to hold the substrate and press the substrate against said polishing surface; and
    the eddy current sensor as recited in claim 1.

6. A substrate deposition apparatus comprising:
    a substrate deposition device configured to deposit a conductive film on the substrate; and
    the eddy current sensor as recited in claim 1.

7. The eddy current sensor as recited in claim 1, further comprising:
    a housing made of a material having a high magnetic permeability, said housing accommodating said sensor coil therein, wherein said detection circuit is connected to said sensor coil.

8. The eddy current sensor as recited in claim 1, further comprising:
    a housing made of a material having a high magnetic permeability, said housing accommodating said sensor coil therein, wherein said housing has a cylindrical shape.

9. The eddy current sensor as recited in claim 1, wherein said sensor coil comprises:
    an excitation coil operable to produce an eddy current in the conductive film; and
    a detection coil operable to detect the eddy current produced in the conductive film.

10. The eddy current sensor as recited in claim 9, wherein said sensor coil further comprises a balance coil operable to adjust a zero point of a detection output in cooperation with said detection coil.

11. The eddy current sensor as recited in claim 1, further comprising:
    a housing made of a material having a high magnetic permeability, said housing accommodating said sensor coil therein, wherein said housing is disposed within a conductive member.

12. The eddy current sensor as recited in claim 1, further comprising:
    an insulating member accommodating said sensor coil therein, said insulating member being embedded in a conductive material, wherein said detection circuit is connected to said sensor coil.

13. An eddy current sensor comprising:
    a sensor coil disposed near a first conductive film formed on a substrate;
    a signal source configured to supply an AC signal to said sensor coil to produce an eddy current in the first conductive film;
    a detection circuit operable to detect the eddy current produced in the first conductive film based on an impedance as viewed from said sensor coil; and
    a controller configured to specify first impedance coordinates of a resistance component and a reactance component of the impedance in rectangular coordinates and to perform phase rotation, parallel displacement, and expansion on the first impedance coordinates,
    wherein the controller is configured to perform phase rotation to conform second impedance coordinates of an impedance of a second conductive material to an axis of the rectangular coordinates and expansion to obtain a change of the first impedance coordinates of the impedance of the first conductive material in an enlarged manner when the first impedance coordinates are influenced by the second impedance coordinates.

14. The eddy current sensor as recited in claim 13, wherein the second conductive film comprises a semiconductor wafer, wherein the first conductive film comprises a barrier layer or a metal film formed on the semiconductor wafer.

15. An eddy current sensor comprising:
    a sensor coil disposed near a conductive film formed on a substrate;
    a signal source configured to supply an AC signal to said sensor coil to produce an eddy current in the conductive film;
    a detection circuit operable to detect the eddy current produced in the conductive film based on an impedance as viewed from said sensor coil; and
    a controller configured to specify an impedance coordinates of a resistance component and a reactance component of the impedance in rectangular coordinates and to move the impedance coordinates on a semicircular locus in the rectangular coordinates according to progress of a process,
    wherein said controller is configured to calculate a change of the film thickness of the conductive film based on length of an arc on which the impedance coordinates move.

16. The eddy current sensor as recited in claim 15, wherein the substrate is held by a substrate holding device having a conductive member located away from said sensor coil so that the conductive member has no influence on the eddy current produced in the conductive film.

17. The eddy current sensor as recited in claim 15, wherein the length of the arc is not influenced by conductivity of the substrate.

18. The eddy current sensor as recited in claim 15, wherein the impedance dramatically varies along one of axes in the rectangular coordinates,
   wherein said controller is configured to select the one of the axes in the rectangular coordinates.

19. The eddy current sensor as recited in claim 15, wherein the impedance coordinates are configured to be set by an offset, an amplification degree, phase rotation, or polarity selection of a main amplifier.

20. The eddy current sensor as recited in claim 15, wherein said controller is configured to measure the impedance coordinates every predetermined time and to detect an endpoint of a process based on a correlation between an impedance characteristic and model data.

21. The eddy current sensor as recited in claim 15, wherein said controller is configured to predict a remaining time until an endpoint of a process.

22. An eddy current sensor comprising:
   a sensor coil disposed near a conductive film formed on a substrate;
   a signal source configured to supply an AC signal to said sensor coil to produce an eddy current in the conductive film;
   a detection circuit operable to detect the eddy current produced in the conductive film based on an impedance as viewed from said sensor coil;
   a storage device operable to store a correction coefficient according to a deposition condition of the conductive film; and
   a controller configured to specify a point including a resistance component and a reactance component of the impedance in rectangular coordinates and to correct the point by the correction coefficient stored in said storage device,
   wherein said controller is configured to remove a resistance component and a reactance component of the impedance due to a substrate material in the substrate having no conductive film, from measurement results, said resistance component and said reactance component of the impedance due to the substrate material in the substrate having no conductive film being previously measured.

23. The eddy current sensor as recited in claim 22, wherein said controller is configured so that the resistance component and the reactance component are constant when film thickness of a reference conductive film is measured.

24. An eddy current sensor comprising:
   a sensor coil disposed near a substrate having a plurality of zones;
   a signal source configured to supply an AC signal to said sensor coil to produce an eddy current in the substrate;
   a detection circuit operable to obtain signal data on the eddy current produced in the plurality of zones of the substrate; and
   a controller configured to detect an endpoint of a process based on the signal data,
   wherein said controller is configured to employ a determination value including a value of signal data on an optimum zone of the plurality of zones, an average value of the signal data on the plurality of zones, an average value of the signal data on a desired combination of the plurality of zones, an effective value, a first time-derivative of the signal data, a second time-derivative of the signal data, and a nth time-derivative of the signal data and to compare the determination value with a predetermined value to detect the endpoint of the process.

25. The eddy current sensor as recited in claim 24, wherein said controller is configured to perform an edge cutting process on the signal data,
   wherein the signal data includes X and Y components of an impedance, a phase $\theta$, a synthesis impedance Z, a frequency F, and a film thickness value converted therefrom.

26. The eddy current sensor as recited in claim 24, wherein said controller is configured to perform an arithmetical operation on a reference time, which is calculated from the signal data, with a coefficient to calculate an additional period of process time and add the additional period of process time to the reference time so as to detect the endpoint of the process.

* * * * *